(12) United States Patent
Matzner et al.

(10) Patent No.: US 11,459,550 B2
(45) Date of Patent: Oct. 4, 2022

(54) MUTATED ARYLSULFATASE A

(71) Applicant: Rheinische Friedrich-Wilhelms-Universität Bonn, Bonn (DE)

(72) Inventors: Ulrich Matzner, Bonn (DE); Volkmar Gieselmann, Alfter (DE)

(73) Assignee: RHEINISCHE FRIRDRICH-WILHELMS-UNIVERSITÄT BONN, Bonn (DE)

( * ) Notice: Subject to any disclaimer, the term of this patent is extended or adjusted under 35 U.S.C. 154(b) by 285 days.

(21) Appl. No.: 16/483,273

(22) PCT Filed: Feb. 5, 2018

(86) PCT No.: PCT/EP2018/052790
§ 371 (c)(1),
(2) Date: Aug. 2, 2019

(87) PCT Pub. No.: WO2018/141958
PCT Pub. Date: Aug. 9, 2018

(65) Prior Publication Data
US 2019/0352624 A1 Nov. 21, 2019

(30) Foreign Application Priority Data
Feb. 3, 2017 (EP) .................................... 17154633

(51) Int. Cl.
*C12N 9/16* (2006.01)
*A61K 38/00* (2006.01)

(52) U.S. Cl.
CPC ........ *C12N 9/16* (2013.01); *C12Y 301/06001* (2013.01); *A61K 38/00* (2013.01)

(58) Field of Classification Search
CPC .............. C12Y 301/06001; C12N 9/16; A61K 38/00
See application file for complete search history.

(56) References Cited

U.S. PATENT DOCUMENTS

| | | | |
|---|---|---|---|
| 6,534,300 | B1 | 3/2003 | Canfield |
| 6,537,785 | B1 | 3/2003 | Canfield |
| 2019/0352624 | A1* | 11/2019 | Matzner ......... C12Y 301/06001 |

FOREIGN PATENT DOCUMENTS

| | | |
|---|---|---|
| JP | 2009/201443 | 9/2009 |
| WO | 2005/073367 | 8/2005 |

OTHER PUBLICATIONS

Matzner et al., "Induction of tolerance to human arylsulfatase A in a mouse model of metachromatic leukodystophy", Molecular medicine, pp. 471-479, Sep. 1, 2007.
International Search Report and Written Opinion, International Patent Application No. PCT/EP2018/052790, dated Jun. 8, 2018 (14 pages).
International Preliminary Report on Patentability issued for International Patent Application No. PCT/EP2018/052790, dated Aug. 6, 2019, 6 pages.

* cited by examiner

*Primary Examiner* — Tekchand Saidha
(74) *Attorney, Agent, or Firm* — Hamre, Schumann, Mueller & Larson, P.C.

(57) ABSTRACT

The present invention pertains to a novel treatment of pathologies caused by an increased synthesis or accumulation of sulfolipids such as sulfatide. The invention provides mutated arylsulfatase A (ARSA or ASA, EC 3.1.6.8) enzymes with increased activity towards sulfatide metabolization. The invention provides nucleic acids encoding the mutant ARSA, the use of the proteins and nucleic acids, as well as pharmaceutical compositions comprising them, in the treatment of lysosomal storage disorders (LSDs) such as metachromatic leukodystrophy (MLD).

20 Claims, 15 Drawing Sheets
Specification includes a Sequence Listing.

Figure 2:

```
human       MGAPRSLLLALAAGLAVAPPNIVLIFADDLSYSDLGCYGHPSQTTPNLDQLAAGGLRFTDFYVP   65
            A  +L LALAAGL+ A PPNI+LIFADDLGYGDLG YGHPS TT NLIQLA GGLRFTDFYVP
mouse       MALGTLFLALAAGLSTAPPNILLIFADDLSYGDLGSYGHPSSTTPNLDQLAEGGLRFTDFYVP   64 human    66 VSLCPPSRAALLTGRLPVRMGMYPGVLVPSSRGGLPLEEVTAEVLAARGYLTGMAGKWH      125
            VSLC PSRAALL GRLPVR  MYPGVL PS +GGLPLEE+T+AEVLAARGYLTGMAGKWH
mouse    65 VSLCPPSRAALLTGRLPVRSAMYPGVLPSSQGGLPLEELTLAEVLAARGYLTGMAGKWH      124 human   126 LGVGPEGARLPPHQGFHRFLGIPYSHDQGPCQNLTCFPPATECLGGCDQGLVPIPRLANL    185
            LGVGPEGA LPPHQGFHRFLGIPYSHDQGPCQNLTCFPP   C GGCDQGLVPIP LANL
mouse   125 LGVGPEGALLPPHQGFHRFLGIPYSHDQGPCQNLTCFPPDFPCKGGCDQGLVPIPLLANL    184 human   186 SVEAQPFWLFGLEARYMAFARDLMADAQRQRPFFLYYASHHTHYPQFSGQSFAERSGRG    245
            +VEAQPPWLPGLEARY++F+ DLMADAQRQ RPFFLYYASHHTHYPQFS QSF +RSGRG
mouse   185 TVEAQPPWLPGLEARYVSFSRDLMADAQPQGRPFFLYYASHHTHYPQFSGQSFTKRSGRG    244 human   246 PFGDSLMELDAAVGLMTAIGDLGLLEEPVIFTADNGPETMRMSRGGCSGLLRCGRGTT     305
            PFGDSLMELD AVG LMT +G LGLLEE VIFTADNGPE MRMS GGCSGLLRCG  TT
mouse   245 PFGDSLMELDGAVGRLMTTVGDLGLLEEPVIFTADNGPELMPMSRGGCSGLLRCGRGTT     304 human   306 YEGGVREPALATWPGHIAPGVTHELASSLDLLPTLAALAGAPLPNVTLDGFDLSPLLIGT    365
            +EGG REPAL +WPGHI PGVTHELASSLDLLPTLAAL GAPLPNVTLDG D+SPLLIGT
mouse   305 FEGGVREPALVYWPGHITPGVTHELASSLDLLPTLAALAGAPLPNVTLDSVDISPLLIGT    364 human   366 GKSPRQSLFFYPSYPDEVRGVFAVRTGKYKAHFFTQGSAHSDTRDPACHASSSLTAREP    425
            GKSPR+S+FFYP YPDE+ GVFAVR GKYKAHFFTQGSAHSDT DPACHA++ LTAHEP
mouse   365 GKSPRKSVFFYPPYPDELRGVFAVRNGKYKAHFFTQGSAHSDTTDPACHAANFLTAHEP    424 flexible
human   426 PLLYDLSKDPGENYNLLGGVAGHTPEVLQALKVLQLLKAQLDAAYTFGPSQVARGEDPAL    485
            PLLYDLS+DPGENYN+L  + G +PE LQALK +QLLKAQ DAA+TFGPSQ+A+GEDPAL
mouse   425 PLLYDLSQDPGENYNVLESIEGSFEALQALKRIQLLKAQYDAATFGPSQIAKGEDPAL     484 human   486 QICCHPGCTPRPACCHCPDPHA   503
            QICC P CTP P CCHCP   +
mouse   485 QICCQPSCTPHPVCCHCPGSQS   502
```

Figure 3:
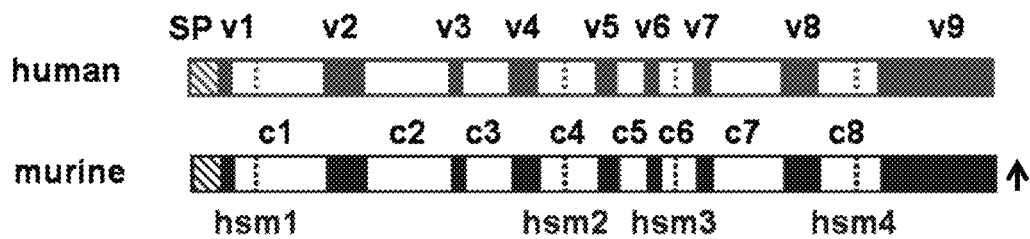
single exchanges of "human specific modifications"
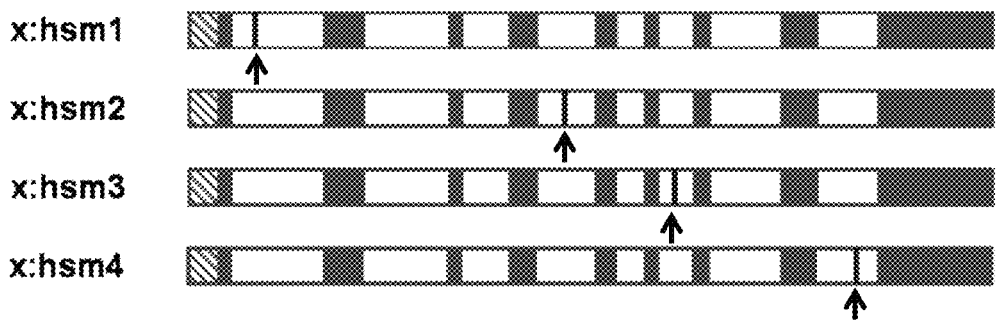
single exchanges of variable domains
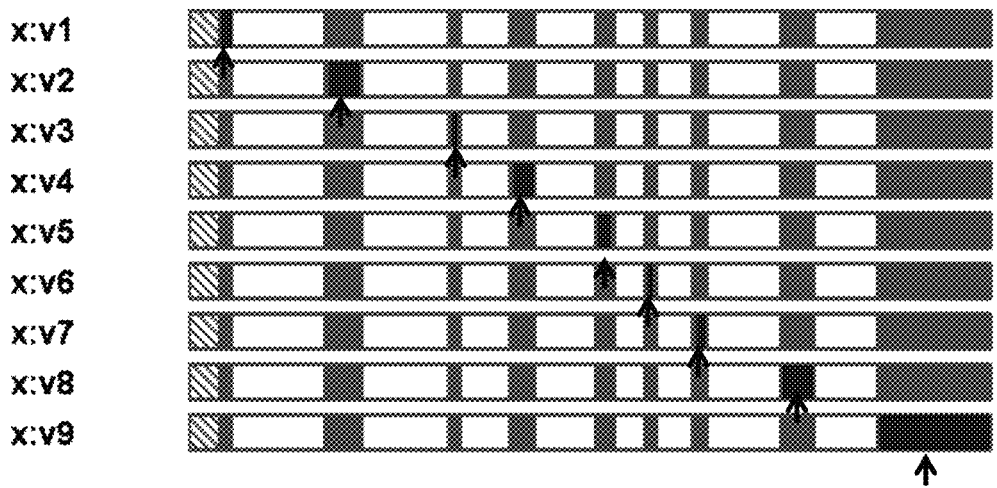

Figure 5:
A:
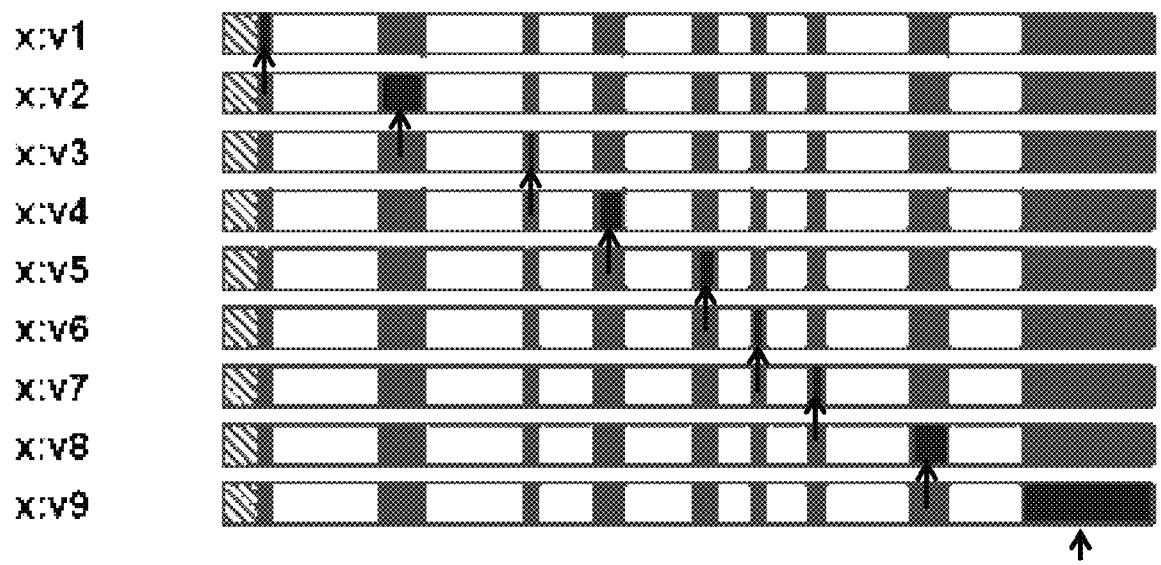
B:
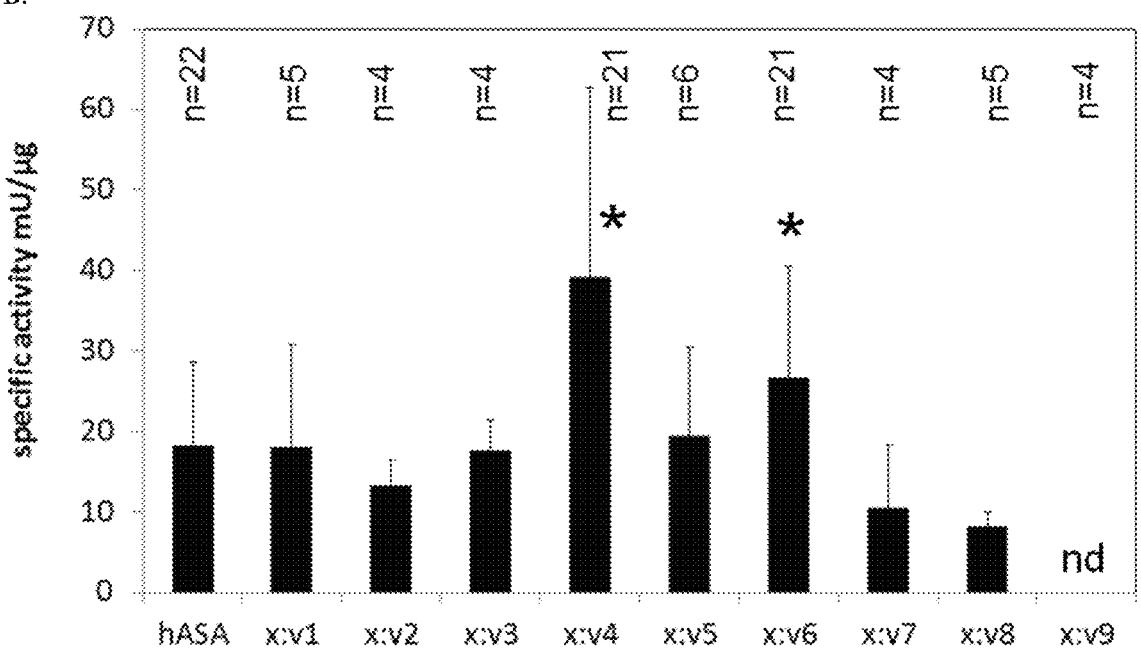
C:
| Student's t-test | P-value | factor |
|---|---|---|
| hASA vs x:v4 | 0.0002 | 2.2 |
| hASA vs x:v6 | 0.0131 | 1.5 |

Figure 6:
(A)
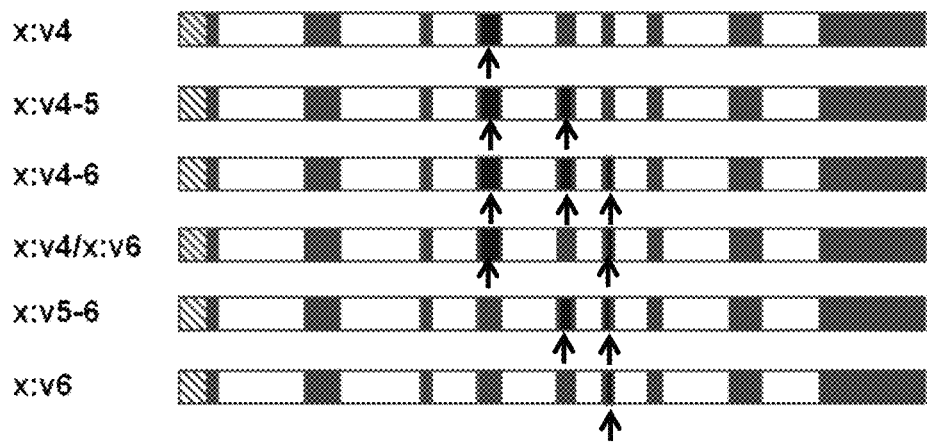
(B)
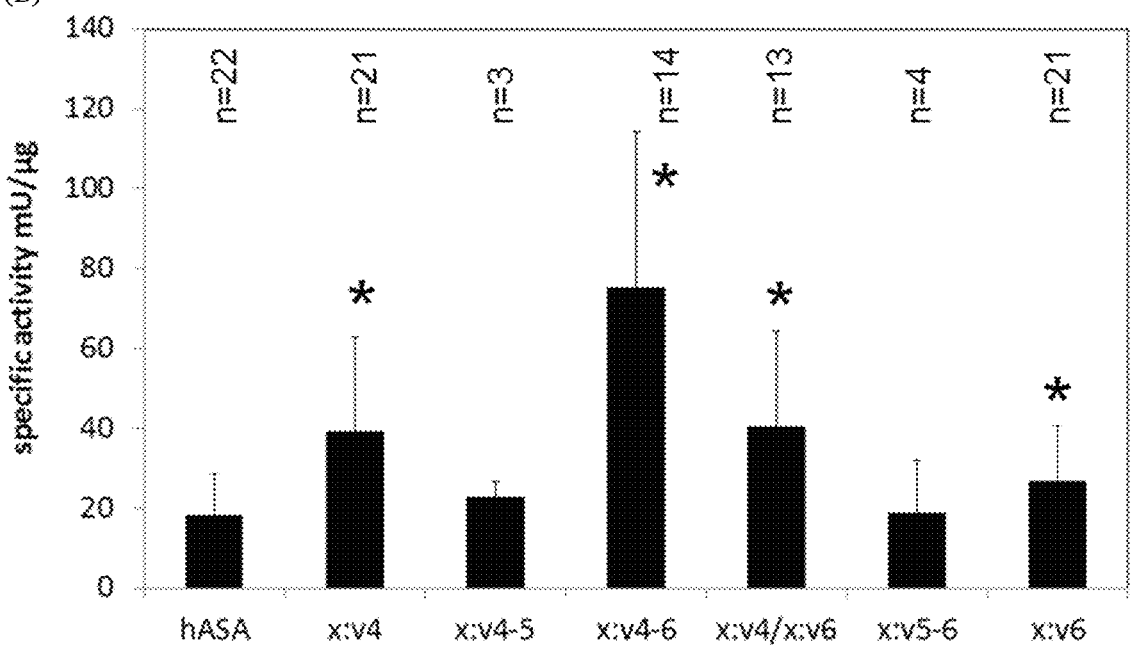
(C)
```
Student's t-test      P-value       factor
hASA vs x:v4          0.0002        2.2
hASA vs x:v6          0.0131        1.5
hASA vs x:v4-6        0.0000004     3.9
hASA vs x:v4/6        0.0012        2.0
```

Figure 10:
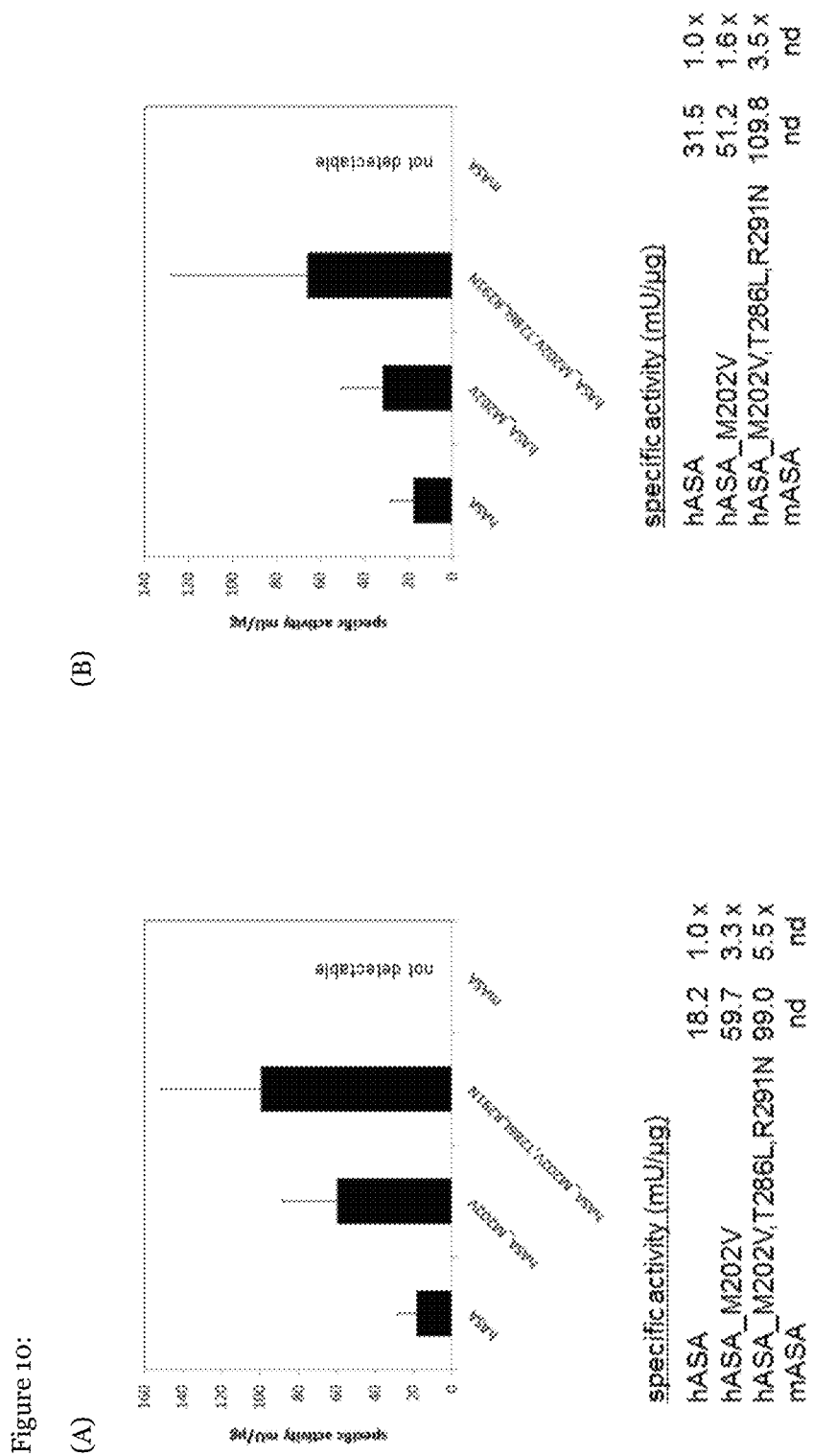

Figure 10 cont.:
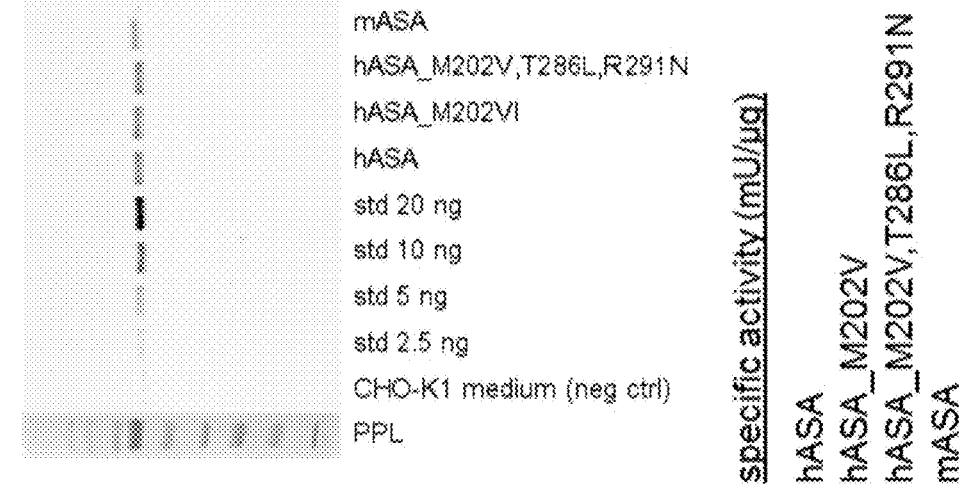
(C)
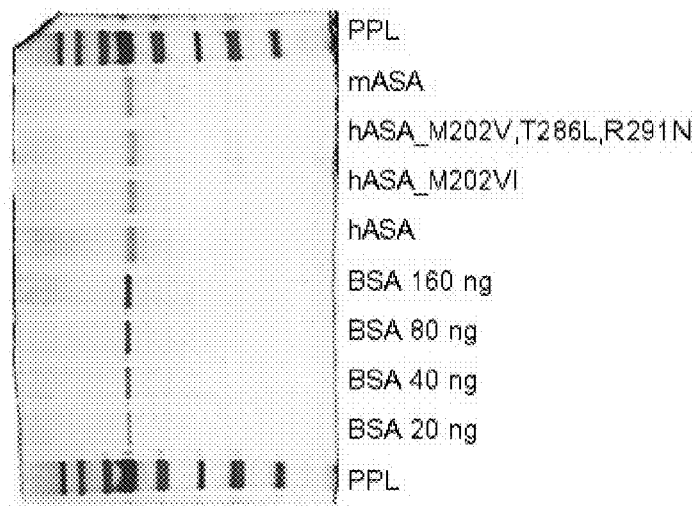
(D)

MUTATED ARYLSULFATASE A

FIELD OF THE INVENTION

The present invention pertains to a novel treatment of pathologies caused by an increased synthesis or accumulation of sulfolipids such as sulfatide. The invention provides mutated arylsulfatase A (ARSA or ASA, EC 3.1.6.8) enzymes with increased activity towards sulfatide metabolization. The invention provides nucleic acids encoding the mutant ARSA, the use of the proteins and nucleic acids, as well as pharmaceutical compositions comprising them, in the treatment of lysosomal storage disorders (LSDs) such as metachromatic leukodystrophy (MLD).

DESCRIPTION

Metachromatic leukodystrophy (MLD) (from the greek word leukos for "white", dys for "lack of", and troph for "growth") is an autosomal recessive lysosomal disorder caused by the deficiency in the enzymatic activity of arylsulfatase A (ARSA or ASA, EC 3.1.6.8), resulting in impaired degradation of 3-O-sulfogalactosylceramide (sulfatide), an essential sphingolipid of myelin (Gieselmann V & Krägeloh-Mann I, Neuropediatrics. 2010, 41, 1-6; Eckhardt M, Mol Neurobiol. 2008, 37: 93-103.). ARSA hydrolyzes sulfatide to galactosylceramide and sulfate and is, due to the lack of alternative degradation pathways, essential for sulfatide recycling. Impairment of ARSA function results in increased accumulation of sulfatide which clinically manifests in progressive demyelination and neurological symptoms resulting in severe debilitation and eventually death of the affected patient. MLD is a rare disorder with a prevalence ranging from 1:40000 to 1:100000. The deficiency in the ARSA enzyme is caused by mutations in the ARSA gene in homo- or heterozygosity encoding ARSA. Many mutations in the ARSA gene have been identified to date, but not all of these mutations cause the deleterious MLD disease. MLD can manifest itself in young children (late-infantile form), where affected children typically begin showing symptoms just after the first year of life (e.g., at about 15-24 months), and death usually occurs about 5 years after onset of clinical symptoms. MLD can manifest itself in children (juvenile form), where affected children typically show cognitive impairment by about the age of 3-10 years, and life-span can vary (e.g., in the range of 10-15 years after onset of symptoms). MLD can manifest itself in adults at various ages beyond puberty (age 16 and later). The progression of such adult-onset forms can vary greatly.

ARSA has been purified from a variety of sources including human liver, placenta, and urine. It is an acidic glycoprotein with a low isoelectric point. Above pH 6.5, the enzyme exists as a monomer with a molecular weight of approximately 60 kDa. ARSA undergoes a pH-dependent polymerisation forming a dimer at pH 4.5. In human urine, the enzyme consists of two non-identical subunits of 63 and 54 kDa. ARSA purified from human liver, placenta, and fibroblasts also consists of two subunits of slightly different sizes varying between 55 and 64 kDa. As in the case of other lysosomal enzymes, ARSA is synthesised on membrane-bound ribosomes as a glycosylated precursor. It then passes through the endoplasmic reticulum and Golgi, where its N-linked oligosaccharides are processed with the formation of phosphorylated mannosyl residues that are required for lysosomal targeting via mannose 6-phosphate receptor binding (Sommerlade et al., J Biol Chem. 1994, 269: 20977-81; Coutinho M F et al., Mol genet metabol. 2012, 105: 542-550).

An unusual protein modification is essential for the enzymatic activity of all 17 human sulfatases known to date. It has been initially identified in ARSA, arylsulfatase B (ARSB) and a sulfatase from the green alga Volvox carteri (Schmidt B et al. Cell. 1995, 82, 271-278, Selmer T et al. Eur J Biochem. 1996, 238, 341-345). This modification leads to the conversion of an active site cysteine residue, which is conserved among the known sulfatases, into a 2-amino-3-oxopropionic acid residue also termed Cα-formylglycine (FGly) (Schmidt B et al. Cell. 1995, 82, 271-278). The formylglycine-generating enzyme (FGE) catalyzes this conversion. A lack of FGE activity causes a combined functional deficiency of all human sulfatases, a severe lysosomal storage disease called multiple sulfatase deficiency (MSD). In ARSA and ARSB the conversion of the Cys-69 and Cys-91 residue, respectively, to FGly is required for generating a catalytically active enzyme. Cys-69 is referred to the precursor ARSA which has an 18 residue signal peptide. In the mature ARSA the mentioned cysteine residue is Cys-51. Further investigations have shown that a linear sequence of 16 residues surrounding the Cys-51 in the mature ARSA is sufficient to direct the conversion and that the protein modification occurs after or at a late stage of co-translational protein translocation into the endoplasmic reticulum when the polypeptide is not yet folded to its native structure (Dierks T et al. Proc Natl Acad Sci. 1997, 94, 11963-1196).

Since MLD is caused by defective ARSA, most therapeutic approaches have tried to correct the biochemical defect by providing wild-type ARSA. The different methods and sources of wild-type ARSA constitute distinct therapeutic approaches (Sevin et al., J Inherit Metab Dis. 2007, 30, 175-83). Hematopoietic stem cell transplantation (HSCT) is the transplantation of hematopoietic stem cells from a healthy donor. After engraftment, progenies of donor-derived cells differentiate into the different cell types of the hematopoeitic system and provide wild-type ARSA to patient's cells via a mannose 6-phosphate-dependent release-recapture pathway. This pathway is based on the pecularities of the sorting process of newly synthesized soluble lysosomal enzymes which may involve partial secretion of newly synthesized lysosomal enzymes and subsequent uptake by neighbouring cells expressing mannose 6-phosphate receptors on the cell surface. Many MLD patients have been treated by allogeneic HSCT with varying success. Enzyme replacement therapy (ERT) relies on providing recombinantly expressed wild-type human ARSA to patients. Repeated intravenous injection of therapeutic enzyme proved to be effective in a number of lysosomal storage diseases and is clinically approved for eight of them. For MLD, two clinical trials using either intravenous or intrathecal infusion of recombinant ARSA have been launched (see below). Also gene therapy approaches are presently in the clinical evaluation. They are generally based on the overexpression of wild-type ARSA in patient's own cells by transducing them with appropriate expression vectors. This can be done either by injecting appropriate expression vectors directly into the tissue (in vivo gene therapy) or by transducing patient's cells outside the body (ex vivo gene therapy). Also in this treatment regimen the overexpressing cells may serve as an enzyme source for deficient cells. An ex vivo gene therapy approach using lentiviral gene transfer to overexpress ARSA in autologous CD34$^+$ hematopoeitic stem cells is in a phase 1/2 clinical trial (see https://clinicaltrials.gov/ct2/show/NCT01560182). The approach was successful in a mouse model of MLD (Biffi A, et al., J Clin Invest. 2004, 113: 1118-29.). In another gene therapy trial (presently recruiting patients) an adenovirus-associated vector encoding wild-type human ARSA will be injected directly into the brain of children affected with early on-set forms of MLD (see https://clinicaltrials.gov/ct2/show/NCT01801709). Also this in vivo gene therapy approach has demonstrated therapeutic benefit in a mouse model of MLD (Piguet F et al. Hum Gene Ther. 2012, 23, 903-14). Other cell based gene therapies for replacing ARSA try to use microencapsulated recombinant cells, oligodendrocyte progenitor cells, and neural progenitor cells as well as embryonic stem cells. All treatment approaches have limitations and bear certain risks. Also producing the enzyme for ERT in high purity and in large scale recombinantly has been a problem. Recently a study of ERT with wild-type ARSA was shown to be effective in MLD (Dali et al., 2016, Mol Gen Metabol. 117, 73). Three cohorts of 6 patients each were treated with 10, 30 or 100 mg of wild-type ARSA every two weeks in a total of 40 weeks treatment schedule. To circumvent the blood-brain barrier, the enzyme was administered into the cerebrospinal fluid via intrathecal injections. Only few immunological adverse effects were observed. Although this phase 1/2 clinical trial did not involve a placebo-treated control group, conclusions can be drawn by comparing the different dose groups. Importantly, the group treated with 100 mg showed a significantly reduced deterioration of motor functions compared to the group treated with 10 mg. However, still treatment effectivity suffers from targeting sufficient enzyme activity to the central nervous system. This is particularly problematic if intravenous injection is used to provide enzyme to the patient as the blood-brain barrier prevents efficient transfer of ARSA from the blood circulation to the brain parenchyma. Preclinical studies in mouse models of MLD had shown that weekly ARSA doses of at least 20 mg per kg body weight are required to improve sulfatide storage in the brain (Matzner et al., Mol Ther, 2009, 17, 600-606). The requirement of high doses in mice explains the failure of a recent clinical trial testing repeated intravenous injection of up to 5 mg/kg ARSA in early-onset MLD (see https://clinicaltrials.gov/ct2/show/results/NCT00418561). The enzyme activity accumulating in the brain might have been below the threshold required for therapeutic effects. Increasing the ARSA-doses is not a preferred solution to increase enzyme levels in the brain and treatment effectivity. Higher enzyme doses are more likely to induce the generation of neutralizing antibodies directed to the expressed protein which might result in severe adverse effects including anaphylaxis. Therefore, there is a need to increase treatment effectivity of ARSA enzyme replacement. The same holds true for gene therapy because a relatively small number of producer cells has to supply ARSA activity to a large number of ARSA-deficient brain cells. In such approaches, an excessive expression of wild-type ARSA might have adverse effects because the overexpressed enzyme can deplete FGE from the endoplasmic reticulum of the producer cells and cause an inefficient post-translational activation of ARSA and other cellular sulfatases. Also the cellular machinery generating mannose 6-phosphate residues might be overloaded, resulting in the delivery of uptake-incompetent enzyme.

The above problems of ERT and gene therapy are solved in a first aspect by providing a mutated ARSA enzyme, or a functional fragment thereof, having increased enzymatic activity compared to the wild-type sequence. The invention therefore pertains in preferred embodiments to a mutated arylsulfatase A (ARSA) enzyme, comprising an amino acid sequence with at least 80%, 85%, 90%, 95%, 96%, 97%, preferably at least 85% or 90% most preferably at least 99% sequence identity to SEQ ID NO: 1 (human ARSA enzyme), wherein the amino acid sequence of the mutated ARSA enzyme, or the functional fragment thereof, when aligned to the sequence of SEQ ID NO: 1, comprises at least one mutation compared to the sequence between residues 100 and 400 of SEQ ID NO: 1.

As used herein, the terms "identical" or percent "identity", when used anywhere herein in the context of two or more nucleic acid or protein/polypeptide sequences, refer to two or more sequences or subsequences that are the same or have (or have at least) a specified percentage of amino acid residues or nucleotides that are the same (i.e., at, or at least, about 60% identity, preferably at, or at least, 65%, 70%, 75%, 80%, 85%, 90%, 91%, 92%, 93% or 94%, identity, and more preferably at, or at least, about 95%, 96%, 97%, 98%, 99%, or higher identity over a specified region—preferably over their full length sequences—, when compared and aligned for maximum correspondence over the comparison window or designated region) as measured using a sequence comparison algorithms, or by manual alignment and visual inspection (see, e.g., NCBI web site). In a particular embodiment, for example when comparing the protein or nucleic acid sequence of a mutated ARSA with wild-type ARSA, the percentage identity can be determined by the Blast searches or local alignments; in particular for amino acid identity, those using BLASTP 2.2.28+ with the following parameters: Matrix: BLOSUM62; Gap Penalties: Existence: 11, Extension: 1; Neighboring words threshold: 11; Window for multiple hits: 40.

The term "mutation" refers to, in the context of a polynucleotide, a modification to the polynucleotide sequence resulting in a change in the sequence of a polynucleotide with reference to a precursor polynucleotide sequence. A mutant polynucleotide sequence can refer to an alteration that does not change the encoded amino acid sequence, for example, with regard to codon optimization for expression purposes, or that modifies a codon in such a way as to result in a modification of the encoded amino acid sequence. Mutations can be introduced into a polynucleotide through any number of methods known to those of ordinary skill in the art, including random mutagenesis, site-specific mutagenesis, oligonucleotide directed mutagenesis, gene shuffling, directed evolution techniques, combinatorial mutagenesis, site saturation mutagenesis among others.

"Mutation" or "mutated" means, in the context of a protein, a modification to the amino acid sequence resulting in a change in the sequence of a protein with reference to a precursor protein sequence. A mutation can refer to a substitution of one amino acid with another amino acid, an insertion or a deletion of one or more amino acid residues. Specifically, a mutation can also be the replacement of an amino acid with a non-natural amino acid, or with a chemically-modified amino acid or like residues. A mutation can also be a truncation (e.g., a deletion or interruption) in a sequence or a subsequence from the precursor sequence. A mutation may also be an addition of a subsequence (e.g., two or more amino acids in a stretch, which are inserted between two contiguous amino acids in a precursor protein sequence) within a protein, or at either terminal end of a protein, thereby increasing the length of (or elongating) the protein. A mutation can be made by modifying the DNA sequence corresponding to the precursor protein. Mutations can be introduced into a protein sequence by known methods in the art, for example, by creating synthetic DNA sequences that encode the mutation with reference to precursor proteins, or chemically altering the protein itself. A "mutant" as used herein is a protein comprising a mutation. For example, it is also possible to make a mutant by replacing a portion of ARSA with a wild-type sequence that corresponds to such portion but includes a desired variation at a specific position that is naturally-occurring in the wild-type sequence.

The use of the mutated ARSA enzymes, or of the functional fragment thereof, of the present invention overcomes the problems in the art because their increased catalytic activity to metabolize sulfatides allows to maintain low enzyme concentrations/expressions while increasing enzyme activity. Also, problems of expressing sufficient amount of enzyme activity either recombinantly (ERT) or in situ (gene therapy) is overcome by the herein provided highly active mutated ARSA variant. The mutated ARSA of the invention shows a up to 5 fold increased activity compared to the human wild-type enzyme.

In preferred embodiments of the invention, the mutated ARSA enzyme amino acid sequence, or of the functional fragment thereof, when aligned to the sequence of SEQ ID NO: 1, comprises at least one mutation compared to the sequence between residues 150 and 350 of SEQ ID NO: 1. More preferably the at least one mutation in the mutated ARSA of the invention is located between residues 180 to 220, and/or 260 to 320 of SEQ ID NO: 1, respectively their corresponding amino acid positions in the mutated sequence. A mutated ARSA is preferred, wherein the amino acid sequence when aligned to the sequence of SEQ ID NO: 1, comprises at least one mutation compared to the sequence between residues 195 to 210, and/or 280 to 300 of SEQ ID NO: 1. In other embodiments the mutated ARSA enzyme amino acid sequence, or of the functional fragment thereof, when aligned to the sequence of SEQ ID NO: 1, comprises at least one mutation at amino acid positions 202, 286 and/or 291 of SEQ ID NO: 1.

A preferred mutated ARSA of the invention is a protein having at least 65%, 70%, 75%, 80%, 85%, 90%, 91%, 92%, 93% or 94%, identity, and more preferably at, or at least, about 95%, 96%, 97%, 98%, 99% or 100% sequence identity compared to the sequence shown in SEQ ID NO: 3 or 4. Also included are functional fragments of these proteins that retain the ARSA catalytic activity. Preferably, however, such mutated ARSA of the invention, or their functional fragments, comprise at least one amino acid mutation at positions corresponding to amino acids 202, 286 and/or 291 of SEQ ID NO: 1.

Therefore also provided in some embodiments is a functional fragment of a mutated ARSA of the invention. The functional fragment preferably comprises, or consists of, or consists essentially of, 50 amino acids, preferably 80, more preferably at least 100, more preferably 200, 300 or 400 or 450 amino acids, under the provision that said functional fragment of a mutated ARSA retains the ARSA catalytic activity as described herein, and preferably comprises at least one amino acid mutation at positions corresponding to amino acids 202, 286 and/or 291 of SEQ ID NO: 1.

As mentioned the mutation introduced into the ARSA according to the invention is preferably selected from a substitution, deletion, addition, insertion or amino acid modification, and preferably is an amino acid substitution. Most preferably, the mutated sequence of the mutated ARSA of the invention constitutes a murinization of the human ARSA amino acid sequence. A "murinization" or "murinizing" in context of the present invention shall be understood to refer to the introduction of a murine ARSA amino acid or nucleic acid sequence into the amino acid or nucleic acid sequence of a homologous non-murine ARSA protein or gene—preferably human ARSA. Therefore, as an example, a human ARSA sequence is considered to be "murinized", if into the human sequence at at least one position the amino acid sequence of the corresponding murine wild type enzyme is introduced. Murinization may include the exchange of only one amino acid from non-mouse to mouse, or of multiple amino acids.

In some embodiments of the invention, the mutated ARSA enzyme amino acid sequence, or of the functional fragment thereof, when aligned to the sequence of SEQ ID NO: 1, comprises at least one mutation selected from M202V, T286L and/or R291N compared to SEQ ID NO: 1, preferably of at least M202V. In other embodiments any one of amino acid substitutions M202V, T286L and/or R291N, may be accompanied by one or more additional amino acid mutations. In other embodiments a mutated ARSA is preferred wherein the mutated ARSA enzyme amino acid sequence, or of the functional fragment thereof, when aligned to the sequence of SEQ ID NO: 1, comprises the mutations selected from the group consisting of M202V, T286L and R291N compared to SEQ ID NO: 1.

A mutated ARSA is preferred wherein the mutated ARSA enzyme amino acid sequence, or of the functional fragment thereof, when aligned to the sequence of SEQ ID NO: 1, comprises at least two mutations, preferably all three, selected from M202V, T286L and/or R291N of SEQ ID NO: 1, preferably of at least M202V.

The mutated ARSA enzyme, or the functional fragment thereof, of the invention in preferred embodiments retains an enzymatic activity of degradation of sulfatides, preferably an activity of degradation of 3-O-sulfogalactosylceramide into galactosylceramide and sulfate. Preferably the mutated ARSA enzyme, or the functional fragment thereof, of the invention has an increased aforementioned activity compared to human wild-type ARSA.

The mutated ARSA of the invention is in preferred embodiments an isolated ARSA or a recombinant ARSA polypeptide. The term "recombinant" or "recombinantly produced" in context of the invention means that a protein or peptide is expressed via an artificially introduced exogenous nucleic acid sequence in a biological cell. Recombinant expression is usually performed by using expression vectors as described herein elsewhere.

In another aspect the problem is solved by an isolated nucleic acid comprising a sequence coding for the mutated ARSA enzyme as described herein before, or for a functional fragment of a mutated ARSA enzyme as described herein before. The term "encoding" or more simply "coding" refers to the ability of a nucleotide sequence to code for one or more amino acids. The term does not require a start or stop codon. An amino acid sequence can be encoded in any one of six different reading frames provided by a polynucleotide sequence and its complement. An amino acid sequence can be encoded by desoxyribonucleic acid (DNA), ribonucleic acid (RNA), or artificially synthesized polymers similar to DNA or RNA.

Another aspect of the invention provides a vector, comprising the nucleic acid of the invention. A "vector" may be any agent that is able to deliver or maintain a nucleic acid in a host cell and includes, for example, but is not limited to, plasmids (e.g., DNA plasmids), naked nucleic acids, viral vectors, viruses, nucleic acids complexed with one or more polypeptide or other molecules, as well as nucleic acids immobilized onto solid phase particles. Vectors are described in detail below. A vector can be useful as an agent for delivering or maintaining an exogenous gene and/or protein in a host cell. A vector may be capable of transducing, transfecting, or transforming a cell, thereby causing the cell to replicate or express nucleic acids and/or proteins other than those native to the cell or in a manner not native to the cell. The target cell may be a cell maintained under cell culture conditions or in other in vivo embodiments, being part of a living organism. A vector may include materials to aid in achieving entry of a nucleic acid into the cell, such as a viral particle, liposome, protein coating, or the like. Any method of transferring a nucleic acid into the cell may be used; unless otherwise indicated, the term vector does not imply any particular method of delivering a nucleic acid into a cell or imply that any particular cell type is the subject of transduction. The present invention is not limited to any specific vector for delivery or maintenance of any nucleic acid of the invention, including, e.g., a nucleic acid encoding a mutant ARSA polypeptide of the invention or a fragment thereof.

Preferably the vector of the invention is an expression vector. The term "expression vector" typically refers to a nucleic acid construct or sequence, generated recombinantly or synthetically, with a series of specific nucleic acid elements that permit transcription of a particular nucleic acid in a host cell. The expression vector typically includes a nucleic acid to be transcribed—the mutated ARSA of the invention—operably linked to a promoter. The term "expression" includes any step involved in the production of the polypeptide including, but not limited to, transcription, post-transcriptional modification, translation, post-translational modification, and/or secretion. A preferred vector of the invention is a plant-specific, bacterial, yeast, insect, vertebrate, preferably mammalian, or a viral vector, preferably retroviral and adeno-associated viral vector. Preferred vectors of the invention are suitable for use in gene therapy, preferably gene therapy based on transformation of autologous adult stem cells.

In another aspect there is also provided a recombinant cell comprising a mutated ARSA enzyme, or the functional fragment thereof, a nucleic acid, or a vector or expression vector of the invention as described herein. A "recombinant cell" or also referred to as "host cell" is any cell that is susceptible to transformation with a nucleic acid. Preferably the recombinant or host cell of the invention is a plant cell, bacterial cell, yeast cell, an insect cell or a vertebrate, preferably a mammalian, cell. A preferred recombinant cell is selected from a cell suitable for recombinant expression of the mutated ARSA of the invention. Most preferred is a Chinese hamster ovary (CHO) cell. Also preferred are human cells, preferably autologous human cells derived from patient suffering from a disease described herein that is treatable with a mutated ARSA of the invention. A preferred human cell is a hematopoietic stem cell (HSC).

In another aspect there is provided a pharmaceutical composition comprising a mutated ARSA enzyme, or the functional fragment thereof, a nucleic acid, a vector, or a recombinant cell of the invention as described before, together with a pharmaceutically acceptable carrier, stabilizer and/or excipient.

In the following the mutated ARSA, nucleic acids encoding the same, vectors and cells comprising these nucleic acids or mutated proteins, as well as pharmaceutical compositions thereof, will be referred to generally as "compounds of the invention".

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intracerebroventricular, intraparenchymal, intra-arterial, intravenous, intradermal, subcutaneous, oral, transdermal (topical) and transmucosal administration. The term "intrathecal," as used herein, means introduced into or occurring in the space under the arachnoid membrane which covers the brain and spinal cord. The term "intracerebroventricular" refers to administration of a composition into the ventricular system of the brain, e.g., via injection, infusion, or implantation (for example, into a ventricle of the brain). As used herein, the term "intraparenchymal" can refer to an administration directly to brain tissue. In other instances, intraparenchymal administration may be directed to any brain region where delivery of one or more compounds of the invention is effective to mitigate or prevent one or more of disorders as described herein.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; anti-bacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride, mannitol or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, mannitol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a compound of the invention such as a mutated ARSA) in the required amount in an appropriate solvent with one or a combination of ingredients enumerated above, as required, followed by filtered sterilization. Generally, dispersions are prepared by incorporating the active compound of the invention into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or con-trolled release of the active ingredient. Biodegradable, biocompatible polymers can be used, such as ethylene vinyl acetate, polyanhydrides, polyglycolic acid, collagen, serum albumin, polyorthoesters, polylactic acid, poly(butyl cyanoacrylate), and poly(lactic-coglycolic) acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of ad-ministration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The problem is furthermore solved by a medical use of the compounds of the invention in the treatment of a disease. The disease is preferably a disease characterized by a pathological enzymatic insufficiency of endogenous ARSA. Generally preferred diseases are demyelinating disorders. In other preferred embodiments the disease is a leukodystrophy. A leukodystrophy in context with the present invention is preferably selected from metachromatic leukodystrophy, multiple sulfatase deficiency, Krabbe disease, adrenoleukodystrophy, Pelizaeus-Merzbacher disease, Canavan disease, Childhood Ataxia with Central Hypomyelination or CACH (also known as Vanishing White Matter Disease), Alexander disease, Refsum disease, and cerebrotendinous xanthomatosis. In most preferred embodiments of the invention the disease is metachromatic leukodystrophy (MLD).

Compositions and methods of the present invention may be used to effectively treat individuals suffering from or susceptible to MLD. The terms, "treat" or "treatment", as used herein, refers to amelioration of one or more symptoms associated with the disease, prevention or delay of the onset of one or more symptoms of the disease, and/or lessening of the severity or frequency of one or more symptoms of the disease. Exemplary symptoms include, but are not limited to, intracranial pressure, hydrocephalus ex vacua, accumulated sulfated glycolipids in the myelin sheaths in the central and peripheral nervous system and in visceral organs, progressive demyelination and axonal loss within the CNS and PNS, and/or motor and cognitive dysfunction, like gait disturbances, mental regression, ataxia, loss of speech, spastic tetraparesis, or optic atrophy.

In some embodiments, treatment refers to partially or complete alleviation, amelioration, relief, inhibition, delaying onset, reducing severity and/or incidence of neurological impairment in an MLD patient. As used herein, the term "neurological impairment" includes various symptoms associated with impairment of the central nervous system (brain and spinal cord). In some embodiments, various symptoms of MLD are associated with impairment of the peripheral nervous system (PNS). In some embodiments, neurological impairment in an MLD patient is characterized by decline in gross motor function. It will be appreciated that gross motor function may be assessed by any appropriate method known to the skilled artisan.

In some embodiments, treatment refers to decreased sulfatide accumulation in various tissues. In some embodiments, treatment refers to decreased sulfatide accumulation in brain target tissues, spinal cord neurons, and/or peripheral target tissues. In certain embodiments, sulfatide accumulation is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, sulfatide accumulation is decreased by at least 1-fold, 2-fold, 3-fold, 4-fold, 5-fold, 6-fold, 7-fold, 8-fold, 9-fold or 10-fold as compared to a control. It will be appreciated that sulfatide storage may be assessed by any appropriate method. For example, in some embodiments, sulfatide storage is measured by alcian blue staining. In some embodiments, sulfatide storage is measured by high-performance liquid chromatography, thin layer chromatography or mass spectrometry.

In some embodiments, treatment refers to reduced vacuolization or a reduced number and/or size of alcian blue-positive storage deposits in neurons (e.g. in nuclei of the medulla oblongata and pons, and in several nuclei of midbrain and forebrain,), astrocytes, oligodendroctes, Schwann cells and/or microglial cells. In certain embodiments, vacuolization or storage deposits in these cell types are decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization or storage deposits are decreased by at least 1-fold, 2-fold, 3-fold, 4-fold, 5-fold, 6-fold, 7-fold, 8-fold, 9-fold or 10-fold as compared to a control.

In some embodiments, treatment refers to increased ARSA enzyme activity in various tissues. In some embodiments, treatment refers to increased ARSA enzyme activity in brain target tissues, spinal cord, peripheral nerves and/or other peripheral target tissues. ARSA enzyme activity can be measured by using artificial substrates such as para-nitrocatechol sulfate and 4-methylumbelliferyl sulfate or by using the natural substrate 3-O-sulfogalactosylceramide. In some embodiments, ARSA enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000% or more as compared to a control. In some embodiments, ARSA enzyme activity is increased by at least 1-fold, 2-fold, 3-fold, 4-fold, 5-fold, 6-fold, 7-fold, 8-fold, 9-fold or 10-fold as compared to a control.

In some embodiments, increased ARSA enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, ARSA enzymatic activity is increased in the lumbar region. In some embodiments, increased ARSA enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, 10,000 nmol/hr/mg, or more.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with the same form MLD (e.g., late-infantile, juvenile, or adult-onset form), who is about the same age and/or gender as the individual being treated (to ensure that the stages of the disease in the treated individual and the control individual(s) are comparable.

The individual (also referred to as "patient" or "subject") being treated is an individual (fetus, infant, child, adolescent, or adult human) having MLD or having the potential to develop MLD. The individual can have residual endogenous ARSA expression and/or activity, or no measurable activity. For example, the individual having MLD may have ARSA expression levels that are less than about 30-50%, less than about 25-30%, less than about 20-25%, less than about 10-15%, less than about 5-10%, less than about 0.1-5% of normal ARSA expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

A treatment according to the invention preferably comprises the administration of a therapeutically effective amount of the compound of the invention to a subject in need of the treatment.

Preferred wherein the treatment comprises the intravenous, intracerebral, intrathecal and/or intracerebroventricular injection or infusion of a therapeutically effective amount of the compound to a subject in need of the treatment.

The compounds of the invention for use in therapeutic treatments are administered to a patient suffering from a disorder as mentioned herein, in therapeutically effective doses. As used herein, the term "therapeutically effective dose" intends that dose of ARSA that achieves a therapeutic effect, and is typically in the range of about 0.05 mg/kg to about 1.0 mg/kg/day for both children and adults, and more preferably of about 0.075 mg/kg/day to about 0.3 mg/kg/day. The therapeutic dose of compound of the invention can be administered as a single dose or divided doses given in certain intervals of time, for example as two, three, four or more daily doses. A preferred treatment comprises the administration of 0.1 to 1000 mg of mutated ARSA enzyme, or the functional fragment thereof, of the invention to a subject in need of the treatment, for example once a week, once every two weeks, or once every three weeks, for at least 2, preferably 3, 4, 5, 6, 7, 8, 9, 10, 11, or 12 months, or longer.

In some embodiments, the treatment of the invention is a gene therapy or an enzyme replacement therapy. The replacement enzyme suitable for the invention is preferably a mutant ARSA as described herein before. The replacement enzyme suitable for the present invention may be produced by any available means. For example, replacement enzymes may be recombinantly produced by utilizing a host cell system engineered to express a replacement enzyme-encoding nucleic acid. Where enzymes are recombinantly produced, any expression system can be used. To give but a few examples, known expression systems include, for example, egg, baculovirus, plant, yeast, or mammalian cells.

In some embodiments, mutated ARSA enzymes, or the functional fragments thereof, suitable for the present invention are produced in mammalian cells. Non-limiting examples of mammalian cells that may be used in accordance with the present invention include BALB/c mouse myeloma line (NSO/1, ECACC No:85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al, J. Gen Virol, 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse Sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3 A, ATCC CRL 1442); human lung cells (W138, ATCC CCL 75); human liver cells (Hep G2, HB 8065); mouse mammary tumor (MMT 060562, ATCC CCL51); TRI cells (Mather et al, Annals N.Y. Acad. Sci., 383:44-68, 1982); MRC 5 cells; FS4 cells; and a human hepatoma line (Hep G2).

In some embodiments, the mutated ARSA enzymes, or the functional fragments thereof, delivered using a method of the invention contain a moiety that binds to a receptor on the surface of brain cells to facilitate cellular uptake and/or lysosomal targeting. For example, such a receptor may be the cation—independent mannose-6-phosphate receptor (CI-MPR) which binds the mannose-6-phosphate (M6P) residues. In addition, the CI-MPR also binds other proteins including IGF-II. In some embodiments, a replacement enzyme suitable for the present invention contains M6P residues on the surface of the protein. In some embodiments, a replacement enzyme suitable for the present invention may contain bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosaminei-phosphate from UDP-N-acetylglucosamine to the 6' position of alpha-1,2-linked mannoses on lysosomal enzymes. Methods and compositions for producing and using such enzymes are described by, for example, Canfield et al. in U.S. Pat. Nos. 6,537,785, and 6,534,300, each incorporated herein by reference.

In some embodiments, mutated ARSA enzymes for use in the present invention may be conjugated or fused to a lysosomal targeting moiety that is capable of binding to a receptor on the surface of brain cells. A suitable lysosomal targeting moiety can be IGF-I, IGF-II, RAP, apolipoprotein E, p97, and variants, homologues or fragments thereof (e.g., including those peptide having a sequence at least 70%, 75%, 80%, 85%, 90%, or 95% identical to a wild-type mature human IGF-I, IGF-II, RAP, apolipoprotein E, p97 peptide sequence).

In some embodiments, a therapeutic protein includes a targeting moiety (e.g., a lysosome targeting sequence) and/or a membrane-penetrating peptide. In some embodiments, a targeting sequence and/or a membrane-penetrating peptide is an intrinsic part of the therapeutic moiety (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

A preferred treatment of a LSD of the invention involves gene therapy. Such methods may include the transformation of a human cell with a mutated ARSA and infusion of the so produced cell into a patient according to the above described preferred routes. Preferably gene therapy may comprise obtaining autologous adult stem cells of a patient, preferably HSCs. These cells are in a next step genetically altered to express a mutated ARSA of the invention. Genetically alteration may be achieved by either transforming the cell with an expression vector of the invention, or alternatively, by directly mutating the HSC endogenous ARSA using for example gene editing (e.g. CRISPR/Cas9 approaches). If the endogenous ARSA comprises one or more mutations decreasing ARSA activity and/or expression, the approach also comprises repairing ARSA deficiency by reconstitution of the wild-type sequence at the respective positions. In general the present invention also pertains to methods for generating a mutated ARSA as described before, by providing a target cell which endogenously expresses human ARSA, and introducing the ARSA mutations of the invention into the endogenous human ARSA sequence.

The pharmaceutical compositions according to the invention are in preferred embodiments suitable for CNS delivery of the compounds of the invention.

In another aspect there is also provided a method for producing the compounds of the invention.

In another aspect the invention also pertains to a method for designing and/or producing a mutated ARSA enzyme, or a functional fragment thereof, comprising the steps of
  (a) providing a parent ARSA enzyme-encoding nucleic acid sequence which encodes a parent ARSA enzyme having an amino acid sequence with at least 80%, 85%, 90%, 95%, 96%, 97%, 98%, 99%, preferably 100% sequence identity to SEQ ID NO: 1,
  (b) introducing into said parent ARSA enzyme-encoding nucleic acid sequence at least one mutation, thereby generating a mutated ARSA enzyme(or functional fragment)-encoding nucleic acid sequence, wherein the mutated ARSA enzyme(or functional fragment)-encoding nucleic acid sequence encodes a mutated ARSA enzyme, or functional fragment thereof, comprising a mutated ARSA enzyme amino acid sequence, that, when aligned to the sequence of SEQ ID NO: 1, comprises at least one mutated amino acid residue compared to the sequence of SEQ ID NO: 1 between residues 100 and 400, and wherein said at least one mutated amino acid residue constitutes a mutation when compared to the amino acid sequence of the parent ARSA enzyme,
  (c) Optionally, expressing said mutated ARSA enzyme, or functional fragment thereof, encoding nucleic acid sequence, to obtain a mutated ARSA enzyme, or the functional fragment thereof.

In this aspect the mutated ARSA enzyme amino acid sequence, or amino acid sequence of the functional fragment, when aligned to the sequence of SEQ ID NO: 1, comprises preferably at least one mutation compared to the sequence SEQ ID NO: 1 between residues 150 and 350, preferably between residues 180 to 220, and/or 260 to 320 of SEQ ID NO: 1, more preferably between residues 195 to 210, and/or 280 to 300 of SEQ ID NO: 1, most preferably at amino acid positions 202, 286 and/or 291 of SEQ ID NO: 1.

Figure 1:
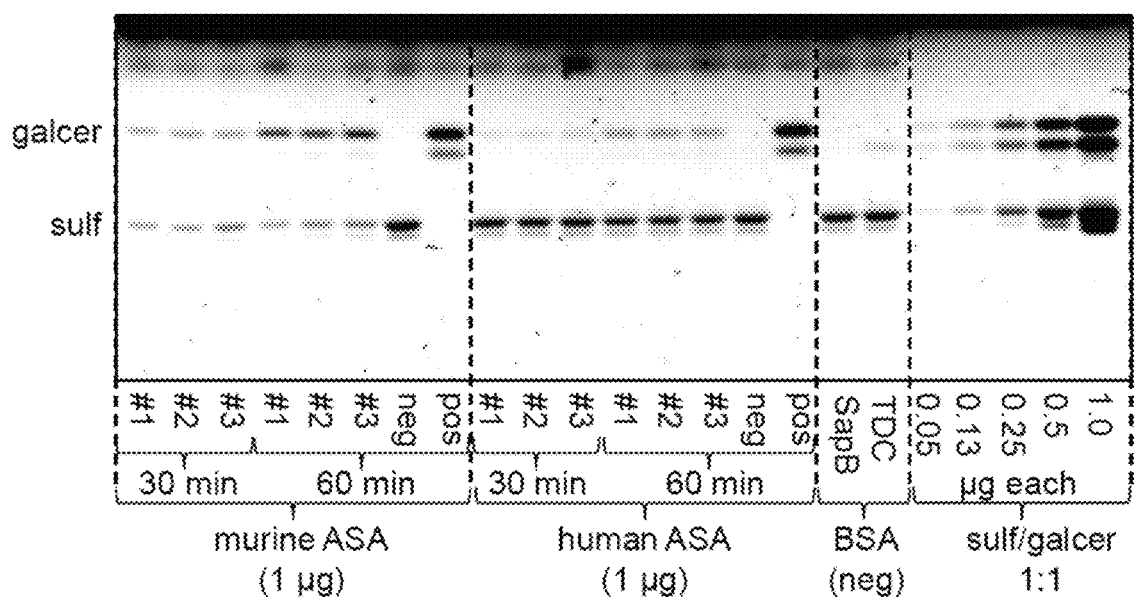

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Activity of murine and human ARSA towards its natural substrate sulfatide (sulf).

FIG. 2: Alignment of the amino acid sequences of human ARSA (SEQ ID NO: 1) and murine ARSA (SEQ ID NO: 5). Sequences are deduced from the cDNAs (Stein C et al., J Biol Chem., 1989, 264, 1252-9; Kreysing et al., Genomics., 1994, 19, 249-56.). Informations about functional and structural elements are from Lukatela et al., Biochemistry, 1998, 37, 3654-64.

FIG. 3: Schematic representation of murinized ARSA constructs with single exchanges of human-specific mutations and variable domains. Black arrows indicate regions where murine sequences were introduced.

Figure 4:
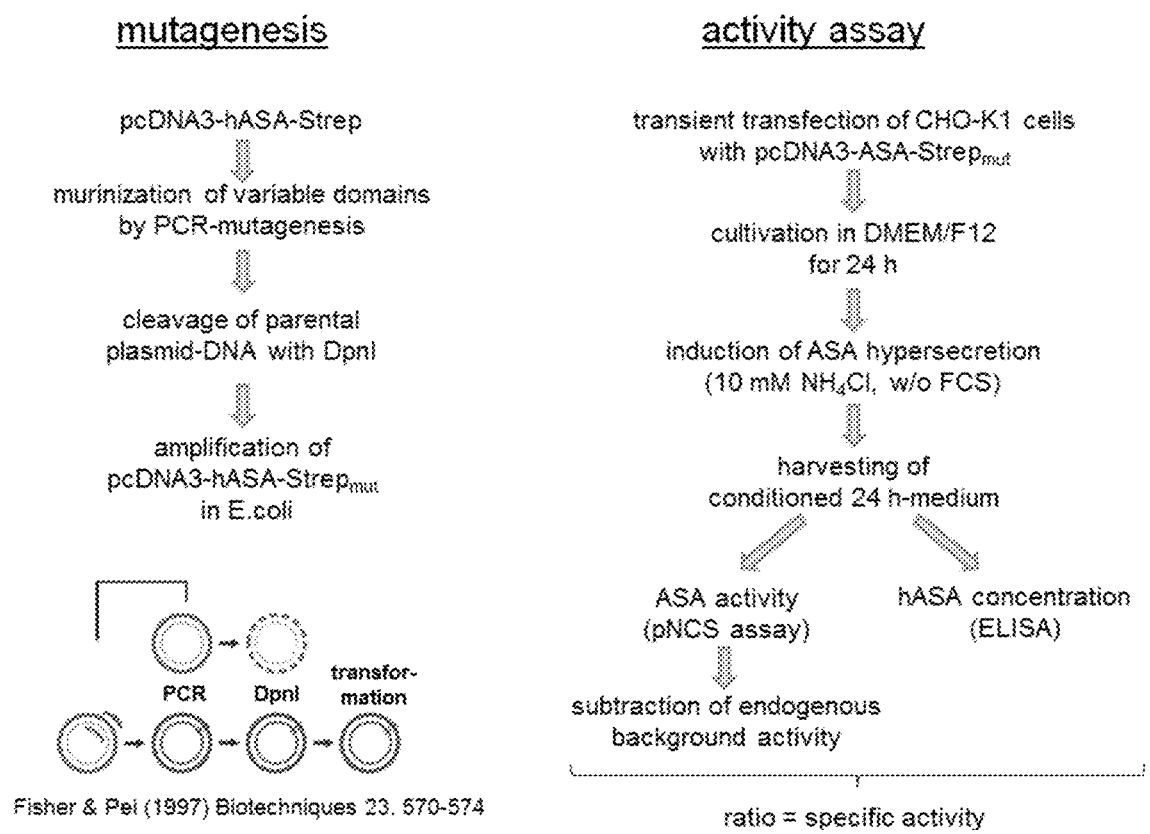

FIG. 4: Illustration of the experimental procedures to generate and analyse chimeric ARSA polypeptides.

FIG. 5: Murinization of individual variable domains. Black arrows indicate regions where murine sequences were introduced.

FIG. 6: Murinization of groups of variable domains. Black arrows indicate regions where murine sequences were introduced.

Figure 7:
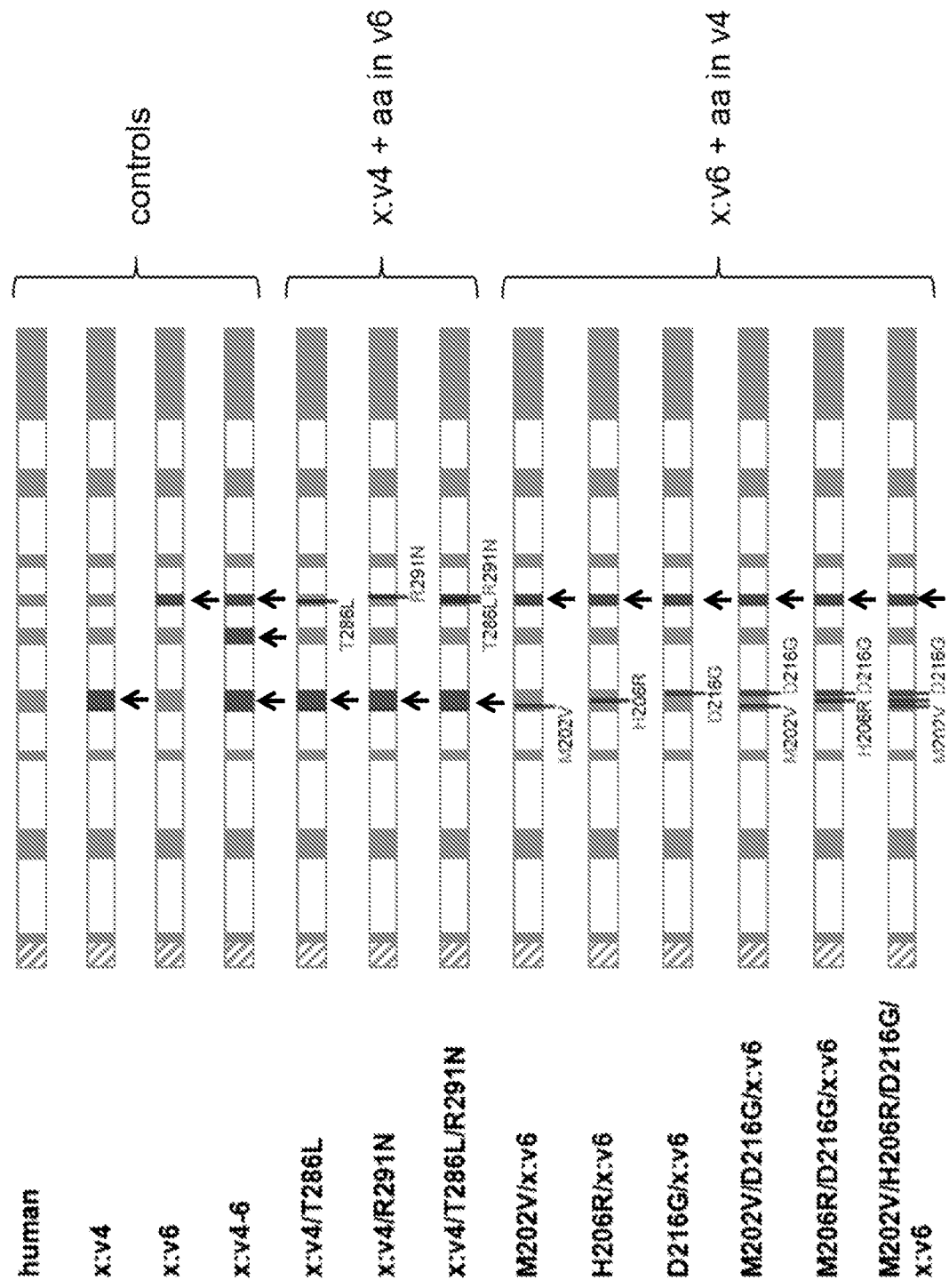
Figure 7:
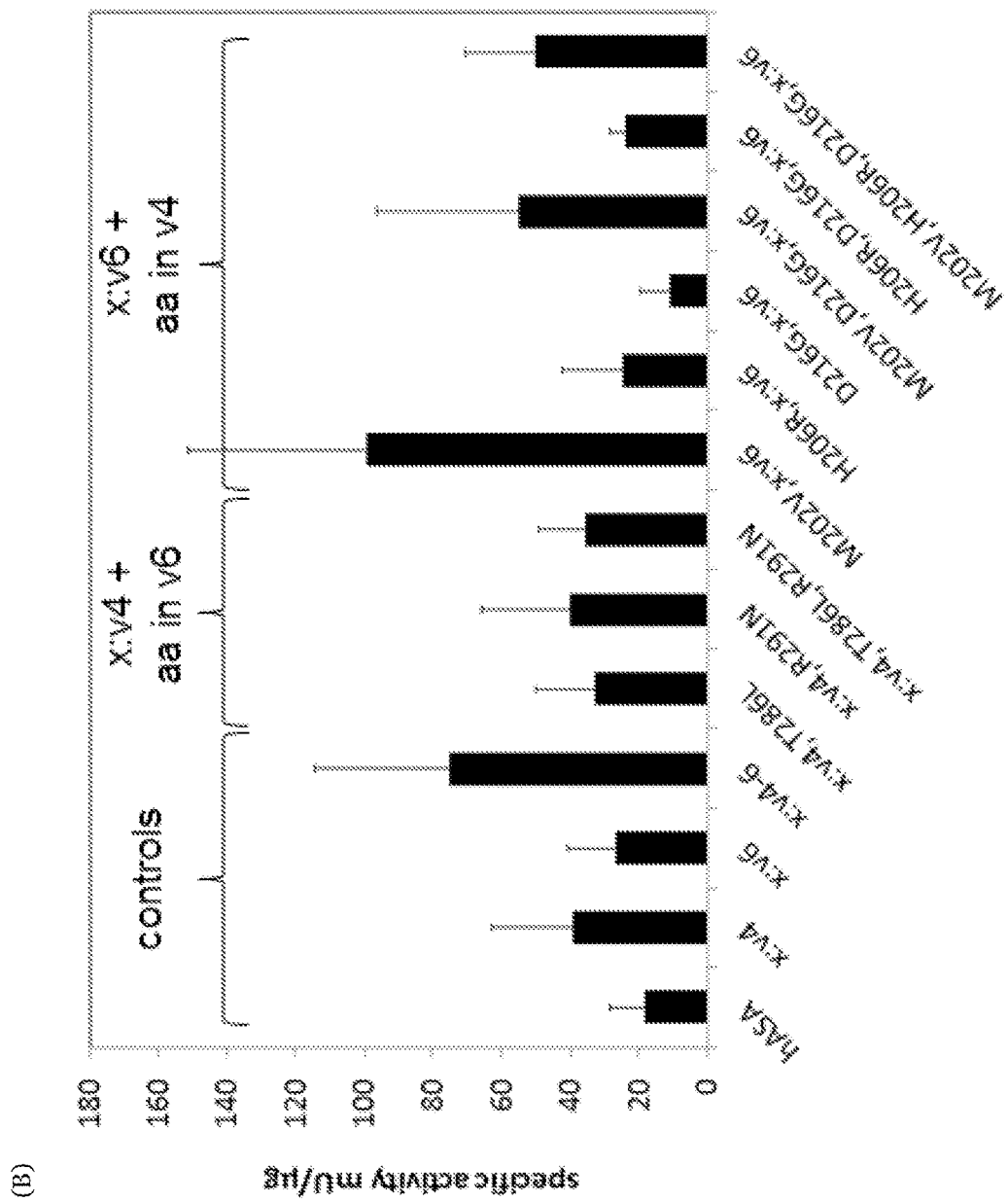

FIG. 7: Murinization of amino acids in the variable domains v4 and v6. Black arrows indicate regions where murine sequences were introduced.

Figure 8:
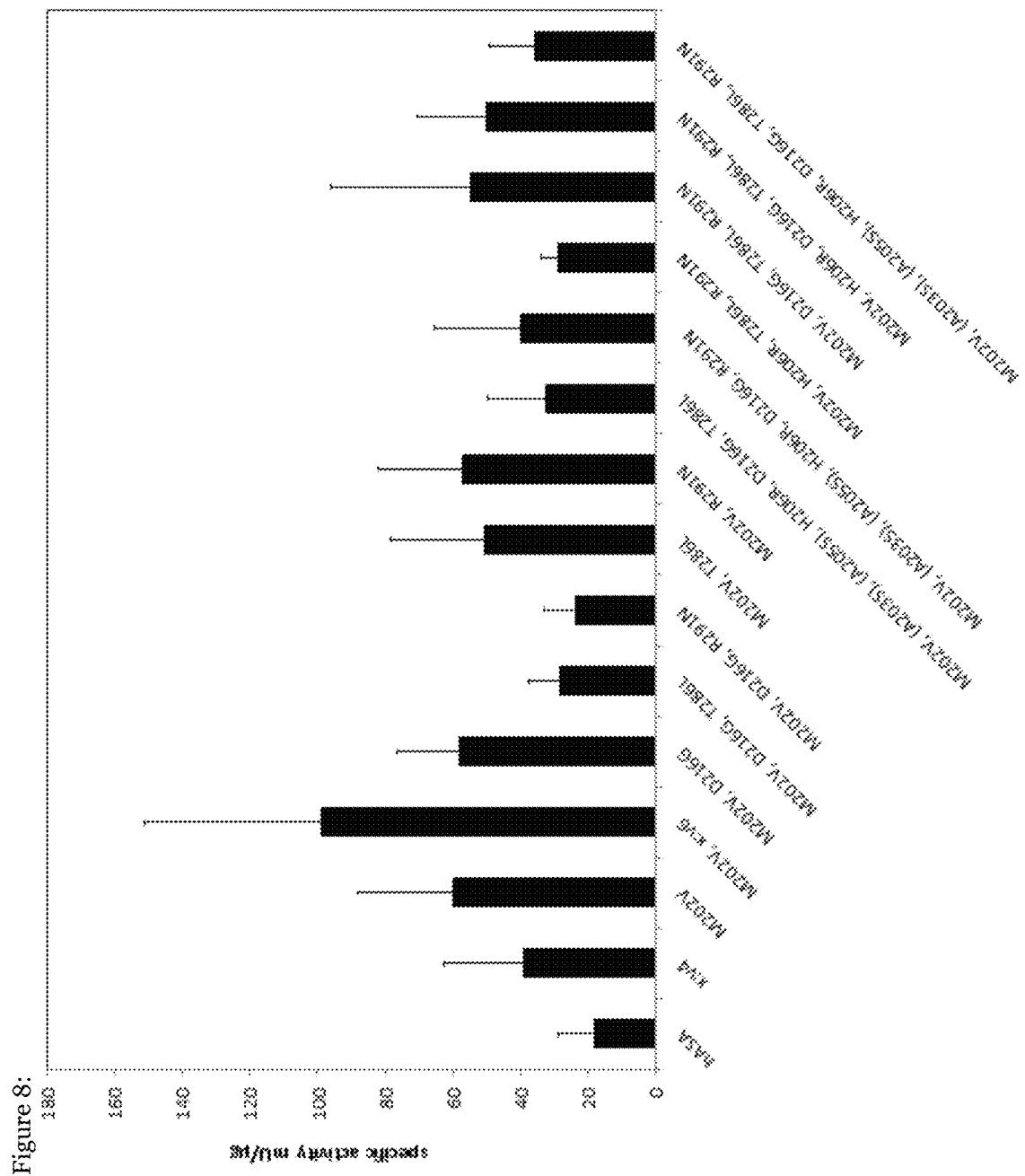

FIG. 8: Murinization of M202 plus other amino acids in v4 or v6.

Figure 9:
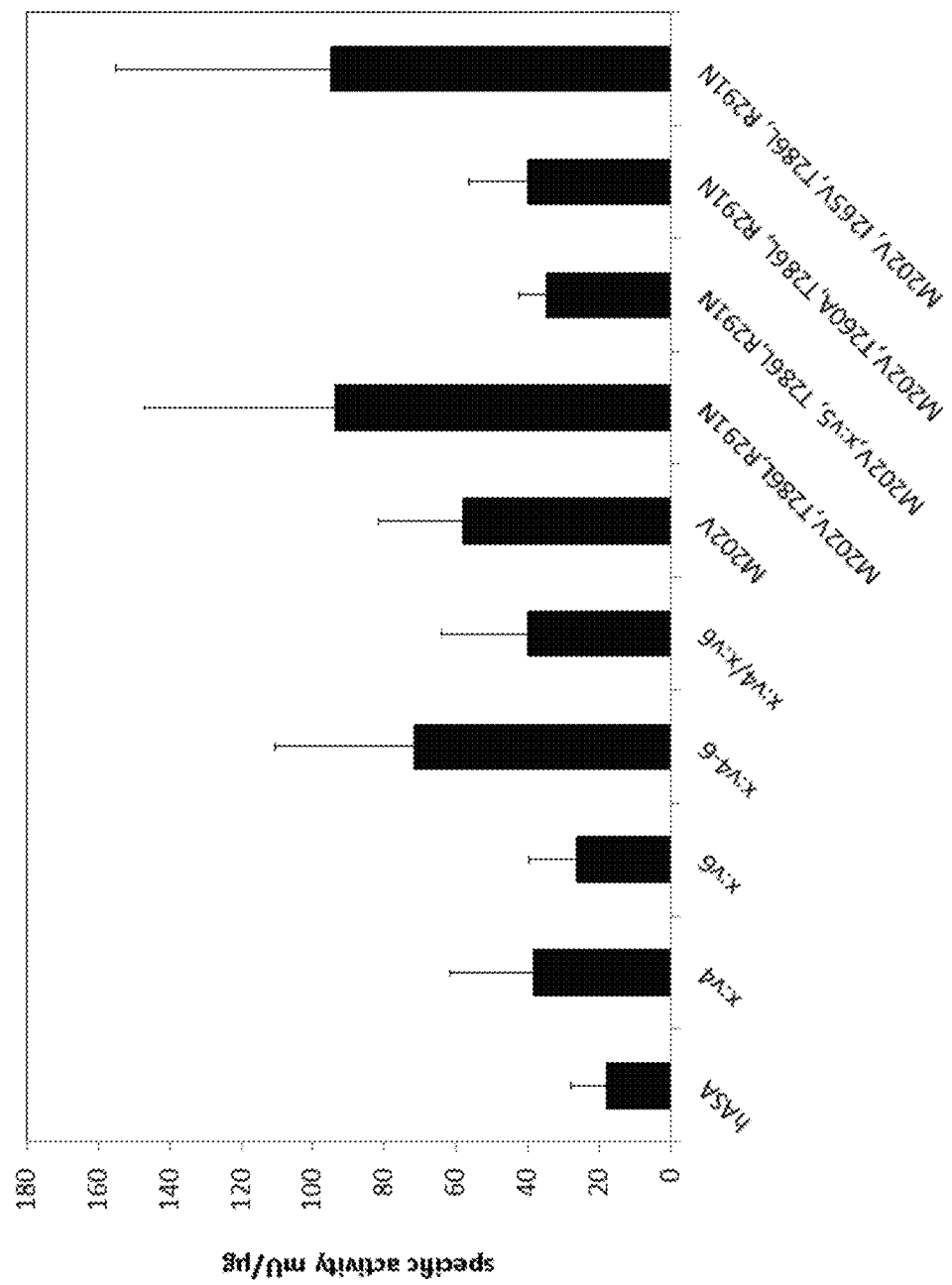

FIG. 9: Partial and complete murinization of v5 in the ARSA mutant M202V, T286L, R291N.

FIG. 10: Specific activities of the ARSA mutants M202V and M202V, T286L, R291N.

Figure 11:
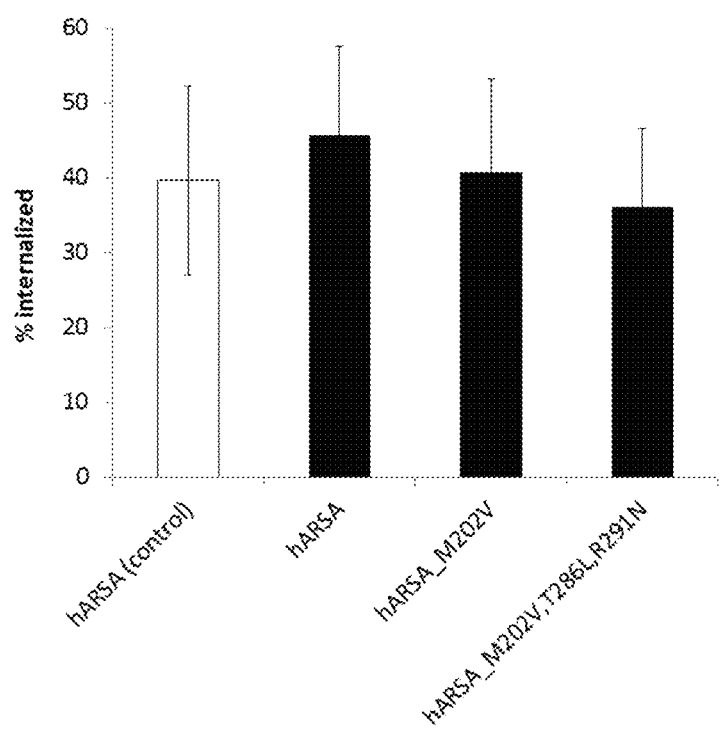

FIG. 11: Endocytosis of ARSA mutants by CHO-K1 cells. Data are based on activity measurements as described in materials and methods. Bars show means±SDs of three independent feeding experiments. A industrially manufactured wildtype human ARSA [hARSA (control)] obtained from Zymenex (HiHerød, Denmark) was used as a control (open bar).

Figure 12:
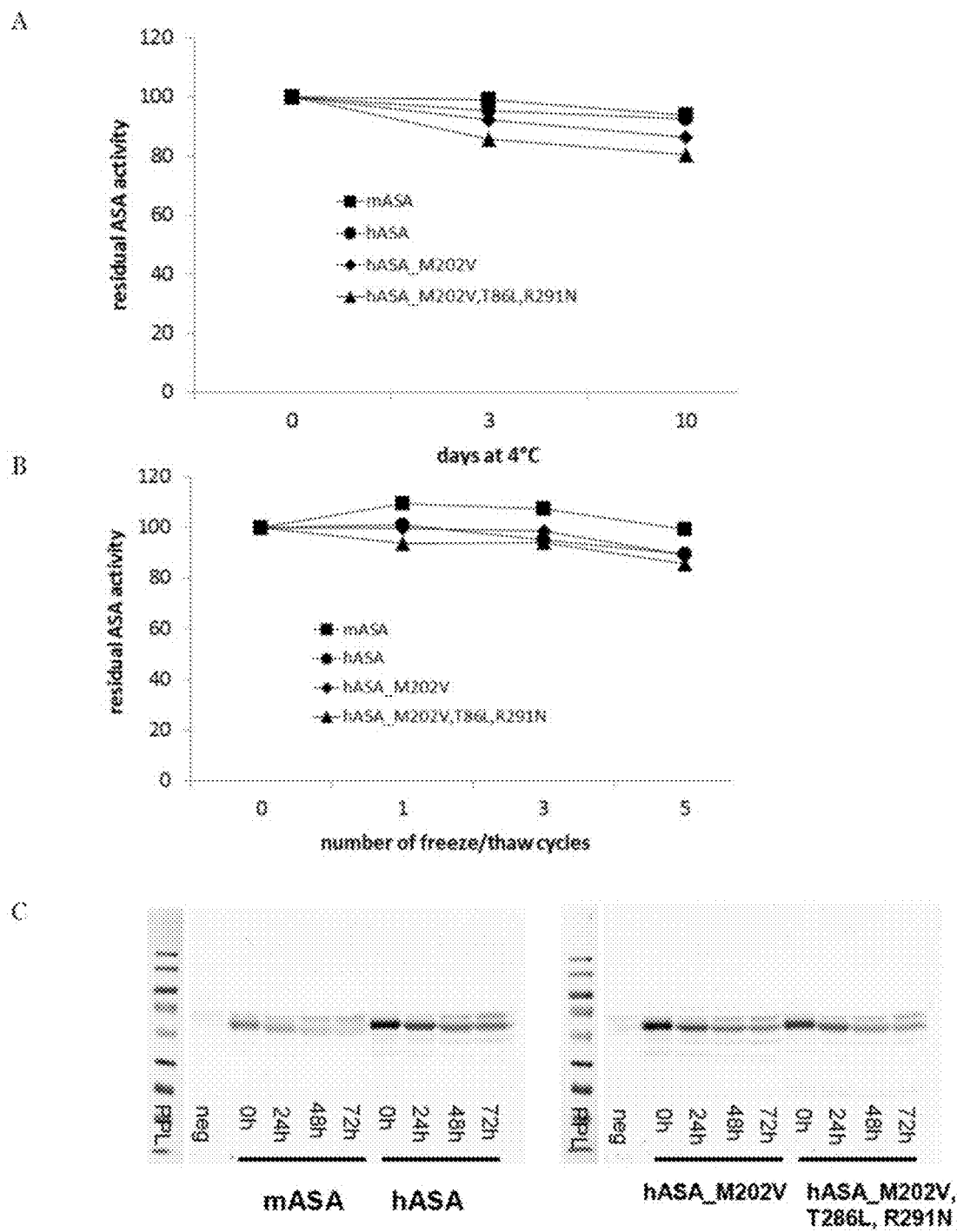

FIG. 12: Stability of ARSA mutants. hASA—human ARSA, mASA—murine ARSA. (A) Shelf lives of the indicated ARSAs after incubation in Tris-buffered saline pH 7.4 for up to 10 days at 4° C. (B) Effect of repeated freeze-thaw cycles on enzyme activity. (C) Intracellular stability. CHO-K1 cells were fed for 24 h with recombinant ARSAs (2.5 µg/ml) as indicated. Then fresh medium was added and the CHO-K1 cells were harvested after chase times of 0, 24, 48 and 72 h, respectively. For Western blotting a mixture of two polyclonal rabbit anti-ARSA antisera was used to detect intracellular murine and human ARSA on the same filter. Homogenates of CHO-K1 cells cultured without ARSA were used as a negative control (neg).

Figure 13:
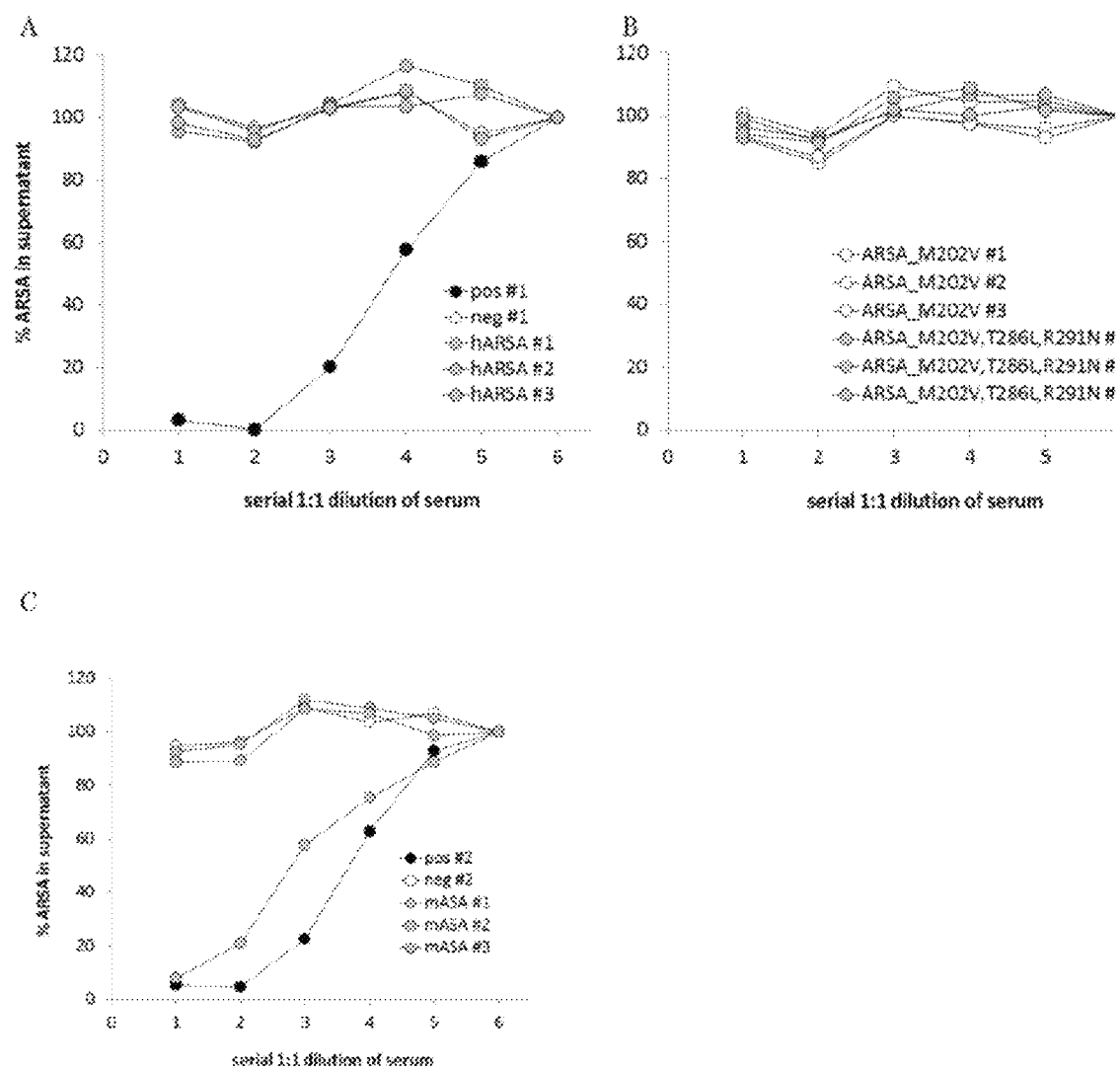

FIG. 13: Anti-ARSA antibodies in serum of humanized MLD mice treated by ERT with different ARSA-variants. Antibody concentrations were measured by immunoprecipitation in sera of 12 mice treated with either human ARSA (hARSA), ARSA_M202V, ARSA_M202V,T286L,R291N or murine ARSA (mARSA) (n=3 mice per group). Two antisera from rabbits that had been immunized with wildtype human ARSA and two sera from mice that had been mock-treated with Tris-buffered saline were taken as positive (pos #1, #2) and negative controls (neg #1, #2), respectively.

SEQ ID NO: 1 shows the sequence of wild type human ARSA protein including the signal peptide (underlined) and most preferred positions for mutation (bold and underlined):

MGAPRSLLLALAAGLAVARPPNIVLIFADDLGYGDLGCYGHPSSTTPNLD
QLAAGGLRFTDFYVPVSLCTPSRAALLTGRLPVRMGMYPGVLVPSSRGGL
PLEEVTVAEVLAARGYLTGMAGKWHLGVGPEGAFLPPHQGFHRFLGIPYS
HDQGPCQNLTCFPPATPCDGGCDQGLVPIPLLANLSVEAQPPWLPGLEAR
YMAFAHDLMADAQRQDRPFFLYYASHHTHYPQFSGQSFAERSGRGPFGDS
LMELDAAVGTLMTAIGDLGLLEETLVIFTADNGPETMRMSRGGCSGLLRC
GKGTTYEGGVREPALAFWPGHIAPGVTHELASSLDLLPTLAALAGAPLPN
VTLDGFDLSPLLLGTGKSPRQSLFFYPSYPDEVRGVFAVRTGKYKAHFFT
QGSAHSDTTADPACHASSSLTAHEPPLLYDLSKDPGENYNLLGGVAGATP
EVLQALKQLQLLKAQLDAAVTFGPSQVARGEDPALQICCHPGCTPRPACC
HCPDPHA

SEQ ID NO: 2 shows the wild type human ARSA encoding nucleic acid sequence (cDNA). The preferred positions for mutations are in bold and underlined.

ATGGGGGCACCGCGGTCCCTCCTCCTGGCCCTGGCTGCTGGCCTGGCCG
TTGCCCGTCCGCCCAACATCGTGCTGATCTTTGCCGACGACCTCGGCTAT
GGGGACCTGGGCTGCTATGGGCACCCCAGCTCTACCACTCCCAACCTGGA
CCAGCTGGCGGCGGGAGGGCTGCGGTTCACAGACTTCTACGTGCCTGTGT
CTCTGTGCACACCCTCTAGGGCCGCCCTCCTGACCGGCCGGCTCCCGGTT
CGGATGGGCATGTACCCTGGCGTCCTGGTGCCCAGCTCCCGGGGGGGCCT
GCCCCTGGAGGAGGTGACCGTGGCCGAAGTCCTGGCTGCCCGAGGCTACC
TCACAGGAATGGCCGGCAAGTGGCACCTTGGGGTGGGGCCTGAGGGGCC
TTCCTGCCCCCCCATCAGGGCTTCCATCGATTTCTAGGCATCCCGTACTC
CCACGACCAGGGCCCCTGCCAGAACCTGACCTGCTTCCCGCCGGCCACTC
CTTGCGACGGTGGCTGTGACCAGGGCCTGGTCCCCATCCCACTGTTGGCC
AACCTGTCCGTGGAGGCGCAGCCCCCTGGCTGCCCGGACTAGAGGCCCG
CTACATGGCTTTCGCCCATGACCTCATGGCCGACGCCCAGCGCCAGGATC
GCCCCTTCTTCCTGTACTATGCCTCTCACCACACCCACTACCCTCAGTTC
AGTGGGCAGAGCTTTGCAGAGCGTTCAGGCCGCGGGCCATTTGGGGACTC
CCTGATGGAGCTGGATGCAGCTGTGGGGACCCTGATGACAGCCATAGGGG
ACCTGGGGCTGCTTGAAGAGACGCTGGTCATCTTCACTGCAGACAATGGA
CCTGAGACCATGCGTATGTCCCGAGGCGGCTGCTCCGGTCTCTTGCGGTG
TGGAAAGGGAACGACCTACGAGGGCGGTGTCCGAGAGCCTGCCTTGGCCT
TCTGGCCAGGTCATATCGCTCCGGCGTGACCCACGAGCTGGCCAGCTCC
CTGGACCTGCTGCCTACCCTGGCAGCCCTGGCTGGGGCCCCACTGCCCAA
TGTCACCTTGGATGGCTTTGACCTCAGCCCCCTGCTGCTGGGCACAGGCA
AGAGCCCTCGGCAGTCTCTCTTCTTCTACCCGTCCTACCCAGACGAGGTC
CGTGGGGTTTTTGCTGTGCGGACTGGAAAGTACAAGGCTCACTTCTTCAC
CCAGGGCTCTGCCCACAGTGATACCACTGCAGACCCTGCCTGCCACGCCT
CCAGCTCTCTGACTGCTCATGAGCCCCGCTGCTCTATGACCTGTCCAAG
GACCCTGGTGAGAACTACAACCTGCTGGGGGGTGTGGCCGGGGCCACCCC
AGAGGTGCTGCAAGCCCTGAAACAGCTTCAGCTGCTCAAGGCCCAGTTAG
ACGCAGCTGTGACCTTCGGCCCCAGCCAGGTGGCCCGGGGCGAGGACCCC
GCCCTGCAGATCTGCTGTCATCCTGGCTGCACCCCCCGCCCAGCTTGCTG
CCATTGCCCAGATCCCCATGCCTGA

SEQ ID NO: 3 shows the amino acid sequence of a mutated ARSA of the invention including one amino acid substitution. The mutation is bold and underlined.

MGAPRSLLLALAAGLAVARPPNIVLIFADDLGYGDLGCYGHPSSTTPNLD
QLAAGGLRFTDFYVPVSLCTPSRAALLTGRLPVRMGMYPGVLVPSSRGGL
PLEEVTVAEVLAARGYLTGMAGKWHLGVGPEGAFLPPHQGFHRFLGIPYS
HDQGPCQNLTCFPPATPCDGGCDQGLVPIPLLANLSVEAQPPWLPGLEAR
YVAFAHDLMADAQRQDRPFFLYYASHHTHYPQFSGQSFAERSGRGPFGDS
LMELDAAVGTLMTAIGDLGLLEETLVIFTADNGPETMRMSRGGCSGLLRC
GKGTTYEGGVREPALAFWPGHIAPGVTHELASSLDLLPTLAALAGAPLPN
VTLDGFDLSPLLLGTGKSPRQSLFFYPSYPDEVRGVFAVRTGKYKAHFFT
QGSAHSDTTADPACHASSSLTAHEPPLLYDLSKDPGENYNLLGGVAGATP
EVLQALKQLQLLKAQLDAAVTFGPSQVARGEDPALQICCHPGCTPRPACC
HCPDPHA

SEQ ID NO: 4 shows the amino acid sequence of a mutated ARSA of the invention including three amino acid substitution. The mutations are bold and underlined.

MGAPRSLLLALAAGLAVARPPNIVLIFADDLGYGDLGCYGHPSSTTPNLD
QLAAGGLRFTDFYVPVSLCTPSRAALLTGRLPVRMGMYPGVLVPSSRGGL
PLEEVTVAEVLAARGYLTGMAGKWHLGVGPEGAFLPPHQGFHRFLGIPYS
HDQGPCQNLTCFPPATPCDGGCDQGLVPIPLLANLSVEAQPPWLPGLEAR
YVAFAHDLMADAQRQDRPFFLYYASHHTHYPQFSGQSFAERSGRGPFGDS
LMELDAAVGTLMTAIGDLGLLEETLVIFTADNGPELMRMSNGGCSGLLRC
GKGTTYEGGVREPALAFWPGHIAPGVTHELASSLDLLPTLAALAGAPLPN
VTLDGFDLSPLLLGTGKSPRQSLFFYPSYPDEVRGVFAVRTGKYKAHFFT
QGSAHSDTTADPACHASSSLTAHEPPLLYDLSKDPGENYNLLGGVAGATP
EVLQALKQLQLLKAQLDAAVTFGPSQVARGEDPALQICCHPGCTPRPACC
HCPDPHA

EXAMPLES

Example 1

Comparison of Human and Murine ARSA Enzyme Activity

The rate of galactosylceramide (galcer) formation was measured by an established micellar assay (Matzner U et al., J Biol Chem, 2009, 284, 9372-81). For the reaction, purified ARSA (ASA, 1 µg) was incubated with 5 nmol sulfatide (sulf) in the presence of 0.33 nmol saposin B (SapB) in 10 mM sodium acetate buffer pH 4.5 at 37° C. Experiments were done in triplicates (#1-3). After incubation times of 30 and 60 min, respectively, lipids were extracted (Folch J et al., J Biol Chem., 1957, 226, 497-509) and separated by thin layer chromatography. Under in vitro conditions, the bile salt taurodeoxycholate (TDC), but not unconjugated deoxycholate, can functionally substitute for SapB. TDC (100 nmol) and deoxycholate (100 nmol) were used instead of SapB in positive (pos) and negative controls (neg), respectively. Results are shown in FIG. 1. Additional negative controls contained 1 µg bovine serum albumin (BSA) instead of ARSA. An equimolar mixture of sulfatide and galactosylceramide (sulf/galcer 1:1) was used as a lipid standard.

The intensity of the galactosylceramide band is a measure for the catalytic rate of ARSA. The densitometric evaluation of the galactosylceramide band (not shown) revealed a 3- to 4-fold higher catalytic rate of murine ARSA compared to human ARSA.

Example 2

Mutagenesis of Human ARSA

In order to identify targets responsible for the increased activity of murine ARSA compared to human ARSA, the amino acid sequences of both enzymes were compared (FIG. 2). Amino acid substitutions tend to occur in clusters defining a mosaic of nine variable and eight constant domains. These are highlighted by bold orange numbers 1-9 (white background) and bold green numbers 1-8 (green background), respectively. Four unclustered amino acid exchanges which are located in constant regions are designated as "human-specific modifications" (hsm's) and are numbered from hsm-1 to hsm-4 (vertical captions in orange). Legend: blue box—signal peptide; red box—alpha helix; red arrow—beta sheat; underlined—surface localization; bold green—important for active site geometry; blue amino acids—conservative exchange (+), red amino acids—non-conservative exchange; red (vertical captions)—amino acid exchanges leading to severe MLD; black (vertical)—MLD with unknown severity; green (vertical)—mild MLD; blue (vertical)—polymorphism.

Using site-directed mutagenesis (see FIG. 3), the variable domains v1 to v9 and the human-specific modifications hsm1 to hsm4 of the human ARSA (dark grey) were exchanged by homologous sequences from the murine ARSA (light grey). The resulting man-mouse chimeric ARSAs were analysed by activity assays as described in FIGS. 4 and 5.

In FIG. 4, left-hand side, a Strep-tag was fused to the N-terminus of the full length human ARSA cDNA and the coding sequence of the Strep-tagged ARSA was inserted into the eukaryotic expression plasmid pcDNA3. Amino acids of the parental construct pcDNA3-ASA-Strep were substituted by their murine homologues using site-directed mutagenesis as indicated.

In FIG. 4, right-hand side: To measure the activity of the murinized ARSA polypeptides, chinese hamster ovary-K1 cells (CHO-K1) were transfected with the mutated expression plasmids pcDNA3-ASA-Strepmut. Binding of the overexpressed ARSA polypeptides to the mannose 6-phosphate receptors was inhibited by addition of 10 mM ammonium chloride. This resulted in the bulk secretion of the newly synthesized lysosomal enzymes and allowed analysis of the murinized ARSAs in the conditioned media. The activity and concentration of the secreted ARSA was measured with the artificial substrate para-nitrocatechol sulfate (Baum H et al., Clin Chim Acta. 1959, 4, 453-455) and a sensitive sandwich ELISA being specific for the human ARSA (Matzner U et al., Gene Ther. 2000, 7, 805-12). To determine the background activity of endogenous hamster-ARSA in the medium, CHO-K1 control cells were transfected with pcDNA3 (empty vector). The specific activity of mutated ARSA (mU/µg) was calculated by subtracting this background activity and dividing the result (mU/ml) through the ARSA concentration (µg/ml).

As shown in FIG. 5, the variable domains v1 to v9 of the human ARSA amino acid sequence (dark grey) were individually exchanged by homologous sequences from the murine ARSA (light grey). The murinized ARSA polypeptides and wild-type ARSA (hASA) were expressed in CHO-K1 cells and their specific activity was determined as described for FIG. 4—results are provided in FIG. 5. Bars represent means±SDs of the indicated number of independent transfection experiments (n=4-22). A statistically significant difference to the wild-type ARSA is indicated by an asterisc (Student's t-test). For respective P-values and fold increases to wild-type ARSA see FIG. 5C. The murinization of the "human-specific modifications" hsm1 to hsm4 (see FIG. 3) had no significant effect on the specific activity of the human ARSA (not shown).

Based on the observation that murinization of either v4 or v6 increased the specific activity of the human ARSA (see FIG. 5), these two and the interjacent variable domain v5 were exchanged by murine sequences (light grey) in the indicated combinations (FIG. 6A). The specific activities of ARSAs with a combined exchange of v4 and v6 or a combined exchange of v4, v5 and v6 are higher than those with single exchanges of v4 and v6 (FIG. 6B). For P-values (Student's t-test) and fold differences to wild-type ARSA see FIG. 6C.

Various combinations of amino acid and domain exchanges were constructed to identify individual amino acids in v4 and v6 that increase the ARSA activity (FIG. 7A). For each murinized position the human amino acid (dark grey), position (black) and murine amino acid (light grey) is shown. A blue box indicates that the entire variable domain was murinized. A combined exchange of human M202 (to murine V202) and human v6 (to murine v6) has the greatest effect and increases the mean specific activity 5.4-fold compared to wild-type human ARSA (FIG. 7B). The difference is statistically significant (Student's t-test; P=6.6×10−8, n=9 and 22, respectively).

The construct M202V, x:v6 combines the three amino acid exchanges M202V, T286L and R291N (FIG. 8). To possibly detect combinations with even higher specific activity, M202V was combined with a variety of individual amino acid exchanges in v4 and v6. Exchanges in brackets are conservative. None of the tested combinations was superior to M202V, x:v6 (=M202V, T286L, R291N). Bars represent means±SDs of the indicated number of n=4-22 independent transfection experiments.

To detect amino acid exchanges in variable domain v5 which might increase the specific activity of M202V, T286L, R291N (=M202V, x:v6) individual amino acids of v5 (T260, I265) or the entire v5-domain was murinized as indicated (FIG. 9). None of the exchanges increased the specific activity compared to M202V, T286L, R291N. Bars represent means±SDs of n=4-22 independent transfection experiments.

Example 3

Specific Activities of ARSA Mutants

To determine the specific activities of the murinized ARSA polypeptides four different methods to measure enzyme concentrations were compared (FIG. 10). The tables indicate the specific activities in mU/μg (first column) and fold increase compared to wild-type ARSA (second column). Human and murine ARSA is abbreviated as hASA and mASA, respectively. Sandwich ELISA of conditoned media using Strep-Tactin to immobilize ARSA via its Strep-tag. A polyclonal anti-human ARSA antiserum was used as secondary antibody (FIG. 10A). Sandwich ELISA using a monoclonal antibody specific for human ARSA as a capture antibody. A polyclonal rabbit anti-human ARSA antiserum was used for detection (FIG. 10B). Silver staining of ARSA polypeptides purified from the conditioned media of transfected CHO-K1 cells via Strep-Tactin affinity chromatography (FIG. 10C). Western blotting of ARSA polypeptides purified from conditioned media of transfected CHO-K1 cells via Strep-Tactin affinity chromatography (FIG. 10D). Peroxidase-conjugated Strep-Tactin was used to visualize the ARSA polypeptides. Depending on the quantification method and the source of enzyme (purified or unpurified) the ARSA mutant M202V,T286L,R291N shows a 5.5 to 2.1-fold increase of specific activity compared to wild-type ARSA.

Example 4

Endocytosis of Mutated ARSA

In preparation of a proof-of-concept study demonstrating increased therapeutic efficacy of the hyperactive ARSA mutants additional experiments were conducted. In particular, the endocytosis, stability and immunogenicity of the hyperactive ARSA mutants were analysed. Furthermore, the recombinant ARSAs were purified in milligram amounts being sufficient for a preclinical enzyme replacement trial in the near future. For this purpose, ARSA_M202V and ARSA_M202V,T286L,R291N were continuously expressed over 6 months as Strep-tagged recombinant proteins by Chinese hamster ovary (CHO) suspension cells and isolated from the conditioned medium by affinity chromatography. In parallel, similar amounts of Strep-tagged wildtype human ARSA and Strep-tagged wildtype murine ARSA were purified as controls.

Enzyme replacement therapy depends on efficient uptake of the infused lysosomal enzyme by the enzyme-deficient cells of the patient. ARSA is primarily endocytosed via mannose 6-phosphate receptors that recognize mannose 6-phosphate residues that are attached to the N-glycans of the enzyme during its synthesis in the endoplasmic reticulum and Golgi apparatus. To analyse a possible adverse effect of the mutations on this posttranslational modification and the endocytic rate, CHO-K1 cells were fed with recombinantly expressed ARSA mutants or wildtype human ARSA for 24 h and the amount of internalized ARSA was determined by activity measurements. No significant difference in the endocytosis of wildtype human ARSA, ARSA_M202V and ARSA_M202V,T286L,R291N was discernible (FIG. 11). The uptake rates were comparable to that of industrially manufactured (and efficiently phosphoryated) human ARSA used in current clinical trials. This suggests a normal mannose 6-phosphorylation of the ARSA mutants.

Example 5

Stability of Mutated ARSA

Higher enzymatic activity can be a consequence of increased conformational flexibility of loop and hinge regions in the polypeptide scaffold promoting the active site dynamics and the velocity of the catalytic cycle. The stability of an enzyme is therefore often inversely correlated with its activity (Miller, S R.; 2017 Evolution 71, 1876-1887). To analyse possible consequences of the activity-promoting amino acid exchanges M202V,T286L and R291N, the stability of the four recombinantly expressed ARSAs in solution (shelf life) and within cells (lysosomal half life) was analysed. Storage in Tris-buffered saline pH 7.4 at 4° C. for up to 10 days diminished the enzyme activities of the recombinant ARSAs by approximately 10% with no clear difference between the four preparations (FIG. 12A). Likewise, repeated freeze-thaw cycles reduced the activities of all four ARSAs slightly and to a similar extent (FIG. 12B). Thus, the mutations did not significantly affect the shelf life of the enzyme. In contrast, clear differences between the ARSA preparations were discernible when their intralysosomal stabilities were determined (FIG. 12C). Pulse feeding experiments revealed half lives of 62 h, 57 h, 46 h and 39 h for wildtype human ARSA, ARSA_M202V, ARSA_M202V,T286L,R291N and wildtype murine ARSA, respectively. Thus, the single mutation M202V and the triple mutation M202V,T286L,R291N diminish in fact the stability of the human ARSA in its normal subcellular environment indicating an inverse correlation between activity and stability. It has to be emphasized, however, that the factor of activity increase (3.4-fold and 5.4-fold, respectively) outweighs by far this loss of stability (8% and 26%, respectively). This can be concluded from the following pharmakinetic considerations: When lysosomal ARSA activity is plotted versus time after dosage, the integral or "area under the curve" is a measure for the bioavailability of ARSA and its potency to degrade sulfatide storage. Taking into account identical endocytic rates (FIG. 11), a mono-exponential decline of lysosomal concentrations (FIG. 12C) and the experimentally determined half lives and factors of activity increase, the areas under the curves are 3.1- and 4.0-fold larger for ARSA_M202V and ARSA_M202V,T286L, R291N compared to wildtype human ARSA (calculation not shown). Thus, the observed decline in stability will only slightly restrict the increased potency of the hyperactive ARSA mutants to hydrolyse sulfatide.

Example 6

Immunogenicity of Mutated ARSA

To analyse possible new epitopes and immunogenicities introduced into the human ARSA polypeptide by the amino acid exchanges, an MLD mouse model was treated by repeated intravenous injections of wildtype human ARSA, ARSA_M202V and ARSA_M202V,T286L,R291N, respectively. Treatments were done in weekly intervals for a total of four weeks (four injections) using 20 mg enzyme per kg body weight in each injection. The ARSA knockout mouse model used for this study was transgenic for an active sitemutant of the human ARSA. This ARSA variant has zero activity and has been constructed by an amino acid exchange in the substrate binding pocket that does not affect the surface structure of the enzyme (Matzner, U., et al. Mol. Med. 13, 471-479; 2007). Consequently, the mouse strain retains its MLD-like phenotype, but does not develop immune reactions to injected wildtype human ARSA. ARSA knockout mice without this transgene show, in contrast, deteriorating adverse reactions with the second injection and more than 50% have died from anaphylactic complications after the fourth injection of 20 mg/kg wildtype human ARSA. By this means, repeated treatment of the immunotolerant mouse strain allows conclusions about possible new immunogenicities of the human ARSA mutants.

Treatment of the immunotolerant mouse model with either wildtype human ARSA, ARSA_M202V or ARSA_M202V,T286L,R291N for four weeks caused no obvious behavioral side effects (n=3 mice per group). Treatment with the murine ARSA, on the contrary, elicited apparent incompatibility reactions such as bristling of the fur, unsteady gait and reduced cage activity. These reactions were transient and occurred 5 to 20 min after treatment in two of the three mice. Signs were observed for the first time after the third and were more pronounced after the fourth injection. The third mouse treated with mARSA showed no behavioral abnormalities except enhanced skin scratching 5 to 10 min after treatment possibly related to histamine-induced itch.

To analyse the development of antibodies to repeatedly infused ARSA, blood was taken three days after the fourth treatment. Antibody titers were measured by the capability of serum to precipitate that recombinant ARSA from solution that had been used for treatment (Matzner, U et al. (2008) J. Mol. Med. (Berl.) 86, 433-442). In this assay, the amount of ARSA lost from the supernatant is a measure for the α-ARSA antibody concentration. Serum from the three mice that had received wildtype human ARSA did not precipitate human ARSA from solution indicating the absence of antibodies and confirming the immunotolerance of the mice (FIG. 13A). Likewise, none of the ARSA_M202V and ARSA_M202V,T286L,R291N treated mice showed antibodies to the ARSA-variant used for treatment (FIG. 13B). Among the three mice treated with murine ARSA, on the contrary, one exhibited a high concentration of antibodies to murine ARSA.

The behavioral and biochemical data indicate that expression of wildtype human ARSA fully protects from immune reactions to ARSA_M202V and ARSA_M202V,T286L, R291N, but only partially to adverse reactions to murine ARSA. Though the mice respond not equally to murine ARSA in this short treatment period of four weeks, it is likely, that they will develop a progressive immune response in the long range. It has to be mentioned that approximately 94% of European MLD patients express human ARSA polypeptides, though at a decreased level or with markedly reduced activity (Polten, A et al (1991). N. Engl. J. Med. 324, 18-22). The preclinical data presented here suggest that ARSA_M202V and ARSA_M202V,T286L,R291N will not cause immunological complications in this majority of patients.

Materials and Methods

Purification of Recombinant ARSAs

For the production of recombinant proteins, CHO-suspension (CHO-S) cells (Thermo Fisher Scientific) were stably transfected with pcDNA3-hARSA-strep, pcDNA3-mARSA-strep, pcDNA3-hARSA_M202V-strep and pcDNA3-hARSA_M202V,T286L,R291N-strep, respectively. Transfection, selection, isolation and screening of single clones as well as production of recombinant ARSA was as described before[3]. Briefly, medium was collected twice a week from Miniperm bioreactors (Sarstedt, Nürnbrecht, Germany) and mixed with 50% (w/v) ammonium sulfate to precipitate ARSA. Precipitates were stored at 4° C.

For affinity purification, the precipitated ARSAs were collected by centrifugation (1,500×g, 4° C., 30 min) and then excessively dialysed against Tris-buffered saline pH 7.4 at 4° C. Insoluble material was removed by centrifugation (100,000×g, 4° C., 60 min) and recombinant ARSA was subsequently purified from the supernatant by affinity chromatography using Strep-Tactin Macroprep® (IBA Lifesciences, Göttingen, Germany) according to the manufacturers recommendations.

Endocytosis and Stability

To determine the endocytic rate of recombinant ARSAs, CHO-K1 cells were cultured for 24 h in cell culture medium to which the respective recombinant ARSA was added at a concentration of 2.5 µg/ml. Then the cells were washed with 1× PBS pH 7.4 and cultured in fresh medium for different chase times. Before harvesting, cells were washed for 3 min at room temperature with 50 mM Glycin, 150 mM NaCl, pH 3.0 to remove surface-bound ARSA. Following trypsinization, cells were spun down and homogenized in 100 µl homogenization buffer (0.5% Triton N-101 in 1× TBS pH 7.0). For endocytosis experiments, cells were harvested immediately after feeding and the ARSA activity of the homogenate was measured. Activities were corrected by subtracting the activitity of CHO-K1 cells cultured without recombinant ARSAs (mean of n=3 dishes) and related to the activity of the incubation medium added to the cells at $t_0$. The lysosomal stability was analysed by Western blotting. For that purpose, aliquots of homogenates (20 µl) or incubation media (4 µl) were separated by SDS-PAGE. ARSA was detected with a mixture of the two polyclonal rabbit antisera #1057 (specific for human ARSA, 1:10.000) and N14 (Santa Cruz Biotechnology, Heidelberg, Germany; sc-79848; detects also murine ARSA; 1:200). The antisera were used in combination with peroxidase-conjugated goat-anti-rabbit (Dianova, Hamburg, Germany; 111-035-003; 1:10.000) as secondary antibody. ARSAs were quantified by densitometry of signals using the image analysis software AIDA (Raytest, Straubenhardt, Germany). Time course data were fitted to the mono-exponential equation $N(t)=N_0\ e^{-\lambda t}$, using the least square method (Microsoft Excel 2010). Half-lives were calculated according to the formula $T_{1/2}=(\ln 2)/\lambda$.

Tolerability Study

ARSA knockout mice being immunotolerant to wildtype human ARSA (Baum, H. et al 1959 Clin. Chim. Acta 4, 453-455.) were treated by repeated intravenous injection of high doses of recombinant ARSAs into the tail vein. For this purpose, four groups of age- and sex-matched immunotolerant ARSA knockout mice (13 months old females, n=3 mice per group) were injected with one recombinant ARSA preparation each using a treatment dose of 20 mg per kg body weight given once a week for a total of four weeks (four injections). A fifth group of mice was mock-treated with buffer (1× TBS pH 7.4) according to the same schedule. Acute immune complications such as scratching, wiping of eyes, bristling of the fur and reduced cage activity were analysed by visual inspection of the mice within the first 30 min after each injection. The formation of antibodies was determined by the ability of serum isolated three days after the fourth treatment to immunoprecipitate the ARSA that has been used for treatment from solution (Matzner, U., et al (2008) J. Mol. Med. (Berl.) 86, 433-442.).

The invention claimed is:

1. An isolated nucleic acid comprising a sequence coding for a mutated arylsulfatase A (ARSA) enzyme, wherein the mutated ARSA enzyme comprises an amino acid sequence with at least 80% sequence identity to SEQ ID NO: 1, wherein the mutated ARSA enzyme amino acid sequence when aligned to the sequence of SEQ ID NO: 1 comprises at least amino acid mutations M202V, T286L and R291N compared to SEQ ID NO: 1.

2. A vector, comprising a nucleic acid, the nucleic acid comprising a sequence coding for a mutated arylsulfatase A (ARSA) enzyme, wherein the mutated ARSA enzyme comprises an amino acid sequence with at least 80% sequence identity to SEQ ID NO: 1, wherein the mutated ARSA enzyme amino acid sequence when aligned to the sequence of SEQ ID NO: 1 comprises at least amino acid mutations M202V, T286L and R291N compared to SEQ ID NO: 1.

3. The vector according to claim 2, which is an expression vector, comprising promoter sequence operably linked to the nucleic acid.

4. A recombinant cell comprising a nucleic acid comprising a sequence coding for a mutated arylsulfatase A (ARSA) enzyme, wherein the mutated ARSA enzyme comprises an amino acid sequence with at least 80% sequence identity to SEQ ID NO: 1, wherein the mutated ARSA enzyme amino acid sequence when aligned to the sequence of SEQ ID NO: 1 comprises at least amino acid mutations M202V, T286L and R291 N compared to SEQ ID NO: 1.

5. The recombinant cell according to claim 4, which is a plant cell, a yeast cell, a bacterial cell, an insect cell, a vertebrate, or a mammalian cell.

6. The isolated nucleic acid according to claim 1, wherein the mutated ARSA enzyme comprises an amino acid sequence at least 80% identical to the sequence of SEQ ID NO: 3 or 4.

7. The isolated nucleic acid according to claim 1, wherein the mutated ARSA enzyme retains an enzymatic activity of degradation of sulfatides.

8. The isolated nucleic acid according to claim 1, wherein the nucleic acid comprises a nucleic acid sequence with at least 80% sequence identity to SEQ ID NO: 2.

9. The isolated nucleic acid according to claim 1, wherein the nucleic acid sequence, when aligned to the sequence of SEQ ID NO: 2, further comprises at least one polynucleotide mutation at nucleic acid positions A604, T605, G606, A856, C857, C858, C871, G872, and/or A873 of SEQ ID NO: 2.

10. The isolated nucleic acid sequences according to claim 9, wherein the at least one polynucleotide mutation is random mutagenesis, site-specific mutagenesis, oligonucleotide directed mutagenesis, gene shuffling, directed evolution techniques, combinatorial mutagenesis, and/or site saturation mutagenesis.

11. The isolated nucleic acid according to claim 9, wherein the nucleotide and/or amino acid mutation constitutes a murinization of a residue in the human ARSA enzyme to a corresponding murine ARSA enzyme residue.

12. The isolated nucleic acid according to claim 1, wherein the nucleic acid is a desoxyribonucleic acid (DNA), a ribonucleic acid (RNA), or an artificially synthesized polymer similar to DNA, RNA, or a complementary DNA (cDNA).

13. The vector according to claim 2, wherein the vector is a plasmid, naked nucleic acid, viral vector, virus, nucleic acid complexed with one or more polypeptide or other molecules, and/or a nucleic acid immobilized on solid phase particles.

14. The vector according to claim 2, wherein the vector comprises a material to aid in achieving entry of the nucleic acid into a cell, or wherein the material is a viral particle, liposome, or protein coating.

15. The vector according to claim 2, wherein the vector is a plant-specific, bacterial, yeast, insect, a vertebrate specific vector, or a mammalian specific vector.

16. The vector according to claim 2, wherein the vector is a viral vector, or wherein the vector is a retroviral and adeno-associated viral vector.

17. The vector according to claim 2, wherein the vector is suitable for use in a gene therapy.

18. The recombinant cell according to claim 4, wherein the recombinant cell is an autologous human cell derived from a patient suffering from a disease that is treatable with the mutated ARSA.

19. The recombinant cell according to claim 5, wherein the mammalian cell is a Chinese Hamster Ovary (CHO) cell, or a hematopoietic stem cell (HSC).

20. The vector according to claim 17, wherein the gene therapy is based on the transformation of autologous adult stem cells.

* * * * *

SEQUENCE LISTING

<160> NUMBER OF SEQ ID NOS: 5

<210> SEQ ID NO 1
<211> LENGTH: 507
<212> TYPE: PRT
<213> ORGANISM: Homo sapiens

<400> SEQUENCE: 1

```
Met Gly Ala Pro Arg Ser Leu Leu Ala Leu Ala Ala Gly Leu Ala
1               5                   10                  15

Val Ala Arg Pro Pro Asn Ile Val Leu Ile Phe Ala Asp Asp Leu Gly
                20                  25                  30

Tyr Gly Asp Leu Gly Cys Tyr Gly His Pro Ser Ser Thr Thr Pro Asn
                35                  40                  45

Leu Asp Gln Leu Ala Ala Gly Gly Leu Arg Phe Thr Asp Phe Tyr Val
        50                  55                  60

Pro Val Ser Leu Cys Thr Pro Ser Arg Ala Ala Leu Leu Thr Gly Arg
65                  70                  75                  80

Leu Pro Val Arg Met Gly Met Tyr Pro Gly Val Leu Val Pro Ser Ser
                85                  90                  95

Arg Gly Gly Leu Pro Leu Glu Glu Val Thr Val Ala Glu Val Leu Ala
                100                 105                 110

Ala Arg Gly Tyr Leu Thr Gly Met Ala Gly Lys Trp His Leu Gly Val
                115                 120                 125

Gly Pro Glu Gly Ala Phe Leu Pro Pro His Gln Gly Phe His Arg Phe
        130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Cys Asp Gln Gly Leu
                165                 170                 175

Val Pro Ile Pro Leu Leu Ala Asn Leu Ser Val Glu Ala Gln Pro Pro
                180                 185                 190

Trp Leu Pro Gly Leu Glu Ala Arg Tyr Met Ala Phe Ala His Asp Leu
                195                 200                 205

Met Ala Asp Ala Gln Arg Gln Asp Arg Pro Phe Phe Leu Tyr Tyr Ala
        210                 215                 220

Ser His His Thr His Tyr Pro Gln Phe Ser Gly Gln Ser Phe Ala Glu
225                 230                 235                 240

Arg Ser Gly Arg Gly Pro Phe Gly Asp Ser Leu Met Glu Leu Asp Ala
                245                 250                 255

Ala Val Gly Thr Leu Met Thr Ala Ile Gly Asp Leu Gly Leu Leu Glu
                260                 265                 270

Glu Thr Leu Val Ile Phe Thr Ala Asp Asn Gly Pro Glu Thr Met Arg
        275                 280                 285

Met Ser Arg Gly Gly Cys Ser Gly Leu Leu Arg Cys Gly Lys Gly Thr
                290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
                325                 330                 335

Leu Pro Thr Leu Ala Ala Leu Ala Gly Ala Pro Leu Pro Asn Val Thr
        340                 345                 350

Leu Asp Gly Phe Asp Leu Ser Pro Leu Leu Leu Gly Thr Gly Lys Ser
                355                 360                 365
```

```
Pro Arg Gln Ser Leu Phe Phe Tyr Pro Ser Tyr Pro Asp Glu Val Arg
        370                 375                 380
Gly Val Phe Ala Val Arg Thr Gly Lys Tyr Lys Ala His Phe Thr
385                 390                 395                 400
Gln Gly Ser Ala His Ser Asp Thr Thr Ala Asp Pro Ala Cys His Ala
                405                 410                 415
Ser Ser Ser Leu Thr Ala His Glu Pro Pro Leu Leu Tyr Asp Leu Ser
            420                 425                 430
Lys Asp Pro Gly Glu Asn Tyr Asn Leu Leu Gly Val Ala Gly Ala
        435                 440                 445
Thr Pro Glu Val Leu Gln Ala Leu Lys Gln Leu Gln Leu Leu Lys Ala
450                 455                 460
Gln Leu Asp Ala Ala Val Thr Phe Gly Pro Ser Gln Val Ala Arg Gly
465                 470                 475                 480
Glu Asp Pro Ala Leu Gln Ile Cys Cys His Pro Gly Cys Thr Pro Arg
                485                 490                 495
Pro Ala Cys Cys His Cys Pro Asp Pro His Ala
                500                 505
```

<210> SEQ ID NO 2
<211> LENGTH: 1524
<212> TYPE: DNA
<213> ORGANISM: Homo sapiens

<400> SEQUENCE: 2

| | | | | |
|---|---|---|---|---|
| atgggggcac | cgcggtccct | cctcctggcc | ctggctgctg | gcctggccgt tgcccgtccg | 60 |
| cccaacatcg | tgctgatctt | tgccgacgac | ctcggctatg | ggacctgggg ctgctatggg | 120 |
| caccccagct | ctaccactcc | caacctggac | cagctggcgg | cgggagggct gcggttcaca | 180 |
| gacttctacg | tgcctgtgtc | tctgtgcaca | ccctctaggg | ccgccctcct gaccggccgg | 240 |
| ctcccggttc | ggatgggcat | gtaccctggc | gtcctggtgc | ccagctcccg gggggggcctg | 300 |
| cccctggagg | aggtgaccgt | ggccgaagtc | ctggctgccc | gaggctacct cacaggaatg | 360 |
| gccggcaagt | ggcaccttgg | ggtgggggcct | gaggggggcct | tcctgccccc ccatcagggc | 420 |
| ttccatcgat | ttctaggcat | cccgtactcc | cacgaccagg | cccctgcca gaacctgacc | 480 |
| tgcttcccgc | cggccactcc | ttgcgacggt | ggctgtgacc | agggcctggt ccccatccca | 540 |
| ctgttggcca | acctgtccgt | ggaggcgcag | ccccctggc | tgcccggact agaggcccgc | 600 |
| tacatggctt | tcgcccatga | cctcatggcc | gacgcccagc | gccaggatcg ccccttcttc | 660 |
| ctgtactatg | cctctcacca | cacccactac | cctcagttca | gtgggcagag ctttgcagag | 720 |
| cgttcaggcc | gcgggccatt | tggggactcc | ctgatggagc | tggatgcagc tgtggggacc | 780 |
| ctgatgacag | ccatagggga | cctggggctg | cttgaagaga | cgctggtcat cttcactgca | 840 |
| gacaatggac | ctgagaccat | gcgtatgtcc | cgaggcggct | gctccggtct cttgcggtgt | 900 |
| ggaaagggaa | cgacctacga | gggcggtgtc | cgagagcctg | ccttggcctt ctggccaggt | 960 |
| catatcgctc | ccggcgtgac | ccacgagctg | gccagctccc | tggacctgct gcctaccctg | 1020 |
| gcagccctgg | ctgggggcccc | actgcccaat | gtcaccttgg | atggctttga cctcagcccc | 1080 |
| ctgctgctgg | gcacaggcaa | gagccctcgg | cagtctctct | tcttctaccc gtcctaccca | 1140 |
| gacgaggtcc | gtgggggtttt | tgctgtgcgg | actggaaagt | acaaggctca cttcttcacc | 1200 |
| cagggctctg | cccacagtga | taccactgca | gaccctgcct | gccacgcctc cagctctctg | 1260 |
| actgctcatg | agccccgct | gctctatgac | ctgtccaagg | accctggtga gaactacaac | 1320 |

```
ctgctggggg gtgtggccgg ggccacccca gaggtgctgc aagccctgaa acagcttcag   1380
ctgctcaagg cccagttaga cgcagctgtg accttcggcc ccagccaggt ggcccggggc   1440
gaggaccccg ccctgcagat ctgctgtcat cctggctgca ccccccgccc agcttgctgc   1500
cattgcccag atccccatgc ctga                                         1524

<210> SEQ ID NO 3
<211> LENGTH: 507
<212> TYPE: PRT
<213> ORGANISM: Homo sapiens

<400> SEQUENCE: 3

Met Gly Ala Pro Arg Ser Leu Leu Leu Ala Leu Ala Ala Gly Leu Ala
1               5                   10                  15

Val Ala Arg Pro Pro Asn Ile Val Leu Ile Phe Ala Asp Asp Leu Gly
            20                  25                  30

Tyr Gly Asp Leu Gly Cys Tyr Gly His Pro Ser Ser Thr Thr Pro Asn
        35                  40                  45

Leu Asp Gln Leu Ala Ala Gly Gly Leu Arg Phe Thr Asp Phe Tyr Val
    50                  55                  60

Pro Val Ser Leu Cys Thr Pro Ser Arg Ala Ala Leu Leu Thr Gly Arg
65                  70                  75                  80

Leu Pro Val Arg Met Gly Met Tyr Pro Gly Val Leu Val Pro Ser Ser
                85                  90                  95

Arg Gly Gly Leu Pro Leu Glu Glu Val Thr Val Ala Glu Val Leu Ala
            100                 105                 110

Ala Arg Gly Tyr Leu Thr Gly Met Ala Gly Lys Trp His Leu Gly Val
        115                 120                 125

Gly Pro Glu Gly Ala Phe Leu Pro Pro His Gln Gly Phe His Arg Phe
    130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Gly Cys Asp Gln Gly Leu
                165                 170                 175

Val Pro Ile Pro Leu Leu Ala Asn Leu Ser Val Glu Ala Gln Pro Pro
            180                 185                 190

Trp Leu Pro Gly Leu Glu Ala Arg Tyr Val Ala Phe Ala His Asp Leu
        195                 200                 205

Met Ala Asp Ala Gln Arg Gln Asp Arg Pro Phe Phe Leu Tyr Tyr Ala
    210                 215                 220

Ser His His Thr His Tyr Pro Gln Phe Ser Gly Gln Ser Phe Ala Glu
225                 230                 235                 240

Arg Ser Gly Arg Gly Pro Phe Gly Asp Ser Leu Met Glu Leu Asp Ala
                245                 250                 255

Ala Val Gly Thr Leu Met Thr Ala Ile Gly Asp Leu Gly Leu Leu Glu
            260                 265                 270

Glu Thr Leu Val Ile Phe Thr Ala Asp Asn Gly Pro Glu Thr Met Arg
        275                 280                 285

Met Ser Arg Gly Gly Cys Ser Gly Leu Leu Arg Cys Gly Lys Gly Thr
    290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
                325                 330                 335
```

-continued

Leu Pro Thr Leu Ala Ala Leu Ala Gly Ala Pro Leu Pro Asn Val Thr
              340                 345                 350

Leu Asp Gly Phe Asp Leu Ser Pro Leu Leu Gly Thr Gly Lys Ser
          355                 360                 365

Pro Arg Gln Ser Leu Phe Phe Tyr Pro Ser Tyr Pro Asp Glu Val Arg
      370                 375                 380

Gly Val Phe Ala Val Arg Thr Gly Lys Tyr Lys Ala His Phe Phe Thr
385                 390                 395                 400

Gln Gly Ser Ala His Ser Asp Thr Thr Ala Asp Pro Ala Cys His Ala
              405                 410                 415

Ser Ser Ser Leu Thr Ala His Glu Pro Pro Leu Leu Tyr Asp Leu Ser
              420                 425                 430

Lys Asp Pro Gly Glu Asn Tyr Asn Leu Leu Gly Gly Val Ala Gly Ala
          435                 440                 445

Thr Pro Glu Val Leu Gln Ala Leu Lys Gln Leu Gln Leu Leu Lys Ala
      450                 455                 460

Gln Leu Asp Ala Ala Val Thr Phe Gly Pro Ser Gln Val Ala Arg Gly
465                 470                 475                 480

Glu Asp Pro Ala Leu Gln Ile Cys Cys His Pro Gly Cys Thr Pro Arg
              485                 490                 495

Pro Ala Cys Cys His Cys Pro Asp Pro His Ala
          500                 505

<210> SEQ ID NO 4
<211> LENGTH: 507
<212> TYPE: PRT
<213> ORGANISM: Homo sapiens

<400> SEQUENCE: 4

Met Gly Ala Pro Arg Ser Leu Leu Leu Ala Leu Ala Ala Gly Leu Ala
1               5                   10                  15

Val Ala Arg Pro Pro Asn Ile Val Leu Ile Phe Ala Asp Asp Leu Gly
              20                  25                  30

Tyr Gly Asp Leu Gly Cys Tyr Gly His Pro Ser Ser Thr Thr Pro Asn
          35                  40                  45

Leu Asp Gln Leu Ala Ala Gly Gly Leu Arg Phe Thr Asp Phe Tyr Val
      50                  55                  60

Pro Val Ser Leu Cys Thr Pro Ser Arg Ala Ala Leu Leu Thr Gly Arg
65                  70                  75                  80

Leu Pro Val Arg Met Gly Met Tyr Pro Gly Val Leu Val Pro Ser Ser
              85                  90                  95

Arg Gly Gly Leu Pro Leu Glu Glu Val Thr Val Ala Glu Val Leu Ala
          100                 105                 110

Ala Arg Gly Tyr Leu Thr Gly Met Ala Gly Lys Trp His Leu Gly Val
      115                 120                 125

Gly Pro Glu Gly Ala Phe Leu Pro Pro His Gln Gly Phe His Arg Phe
130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Gly Cys Asp Gln Gly Leu
              165                 170                 175

Val Pro Ile Pro Leu Leu Ala Asn Leu Ser Val Glu Ala Gln Pro Pro
          180                 185                 190

Trp Leu Pro Gly Leu Glu Ala Arg Tyr Val Ala Phe Ala His Asp Leu
      195                 200                 205

Met Ala Asp Ala Gln Arg Gln Asp Arg Pro Phe Phe Leu Tyr Tyr Ala
            210                 215                 220

Ser His His Thr His Tyr Pro Gln Phe Ser Gln Ser Phe Ala Glu
225                 230                 235                 240

Arg Ser Gly Arg Gly Pro Phe Gly Asp Ser Leu Met Glu Leu Asp Ala
            245                 250                 255

Ala Val Gly Thr Leu Met Thr Ala Ile Gly Asp Leu Gly Leu Leu Glu
            260                 265                 270

Glu Thr Leu Val Ile Phe Thr Ala Asp Asn Gly Pro Glu Leu Met Arg
            275                 280                 285

Met Ser Asn Gly Gly Cys Ser Gly Leu Leu Arg Cys Gly Lys Gly Thr
            290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
            325                 330                 335

Leu Pro Thr Leu Ala Ala Leu Ala Gly Ala Pro Leu Pro Asn Val Thr
            340                 345                 350

Leu Asp Gly Phe Asp Leu Ser Pro Leu Leu Leu Gly Thr Gly Lys Ser
            355                 360                 365

Pro Arg Gln Ser Leu Phe Phe Tyr Pro Ser Tyr Pro Asp Glu Val Arg
            370                 375                 380

Gly Val Phe Ala Val Arg Thr Gly Lys Tyr Lys Ala His Phe Phe Thr
385                 390                 395                 400

Gln Gly Ser Ala His Ser Asp Thr Thr Ala Asp Pro Ala Cys His Ala
            405                 410                 415

Ser Ser Ser Leu Thr Ala His Glu Pro Pro Leu Leu Tyr Asp Leu Ser
            420                 425                 430

Lys Asp Pro Gly Glu Asn Tyr Asn Leu Leu Gly Gly Val Ala Gly Ala
            435                 440                 445

Thr Pro Glu Val Leu Gln Ala Leu Lys Gln Leu Gln Leu Leu Lys Ala
            450                 455                 460

Gln Leu Asp Ala Ala Val Thr Phe Gly Pro Ser Gln Val Ala Arg Gly
465                 470                 475                 480

Glu Asp Pro Ala Leu Gln Ile Cys Cys His Pro Gly Cys Thr Pro Arg
            485                 490                 495

Pro Ala Cys Cys His Cys Pro Asp Pro His Ala
            500                 505

<210> SEQ ID NO 5
<211> LENGTH: 506
<212> TYPE: PRT
<213> ORGANISM: Mus musculus

<400> SEQUENCE: 5

Met Ala Leu Gly Thr Leu Phe Leu Ala Leu Ala Ala Gly Leu Ser Thr
1               5                   10                  15

Ala Ser Pro Pro Asn Ile Leu Leu Ile Phe Ala Asp Asp Leu Gly Tyr
            20                  25                  30

Gly Asp Leu Gly Ser Tyr Gly His Pro Ser Ser Thr Thr Pro Asn Leu
        35                  40                  45

Asp Gln Leu Ala Glu Gly Gly Leu Arg Phe Thr Asp Phe Tyr Val Pro
    50                  55                  60

```
Val Ser Leu Cys Thr Pro Ser Arg Ala Leu Leu Thr Gly Arg Leu
 65              70                  75                  80

Pro Val Arg Ser Gly Met Tyr Pro Gly Val Leu Gly Pro Ser Ser Gln
                 85                  90                  95

Gly Gly Leu Pro Leu Glu Glu Val Thr Leu Ala Glu Val Leu Ala Ala
                100                 105                 110

Arg Gly Tyr Leu Thr Gly Met Ala Gly Lys Trp His Leu Gly Val Gly
            115                 120                 125

Pro Glu Gly Ala Phe Leu Pro Pro His Gln Gly Phe His Arg Phe Leu
130                 135                 140

Gly Ile Pro Tyr Ser His Asp Gln Gly Pro Cys Gln Asn Leu Thr Cys
145                 150                 155                 160

Phe Pro Pro Asp Ile Pro Cys Lys Gly Gly Cys Asp Gln Gly Leu Val
                165                 170                 175

Pro Ile Pro Leu Leu Ala Asn Leu Thr Val Glu Ala Gln Pro Pro Trp
            180                 185                 190

Leu Pro Gly Leu Glu Ala Arg Tyr Val Ser Phe Ser Arg Asp Leu Met
        195                 200                 205

Ala Asp Ala Gln Arg Gln Gly Arg Pro Phe Phe Leu Tyr Tyr Ala Ser
210                 215                 220

His His Thr His Tyr Pro Gln Phe Ser Gly Gln Ser Phe Thr Lys Arg
225                 230                 235                 240

Ser Gly Arg Gly Pro Phe Gly Asp Ser Leu Met Glu Leu Asp Gly Ala
                245                 250                 255

Val Gly Ala Leu Met Thr Thr Val Gly Asp Leu Gly Leu Leu Glu Glu
                260                 265                 270

Thr Leu Val Ile Phe Thr Ala Asp Asn Gly Pro Glu Leu Met Arg Met
            275                 280                 285

Ser Asn Gly Gly Cys Ser Gly Leu Leu Arg Cys Gly Lys Gly Thr Thr
290                 295                 300

Phe Glu Gly Gly Val Arg Glu Pro Ala Leu Val Tyr Trp Pro Gly His
305                 310                 315                 320

Ile Thr Pro Gly Val Thr His Glu Leu Ala Ser Ser Leu Asp Leu Leu
                325                 330                 335

Pro Thr Leu Ala Ala Leu Thr Gly Ala Pro Leu Pro Asn Val Thr Leu
            340                 345                 350

Asp Gly Val Asp Ile Ser Pro Leu Leu Leu Gly Thr Gly Lys Ser Pro
        355                 360                 365

Arg Lys Ser Val Phe Phe Tyr Pro Pro Tyr Pro Asp Glu Ile His Gly
    370                 375                 380

Val Phe Ala Val Arg Asn Gly Lys Tyr Lys Ala His Phe Phe Thr Gln
385                 390                 395                 400

Gly Ser Ala His Ser Asp Thr Thr Ser Asp Pro Ala Cys His Ala Ala
                405                 410                 415

Asn Arg Leu Thr Ala His Glu Pro Pro Leu Leu Tyr Asp Leu Ser Gln
            420                 425                 430

Asp Pro Gly Glu Asn Tyr Asn Val Leu Glu Ser Ile Glu Gly Val Ser
        435                 440                 445

Pro Glu Ala Leu Gln Ala Leu Lys His Ile Gln Leu Leu Lys Ala Gln
    450                 455                 460

Tyr Asp Ala Ala Met Thr Phe Gly Pro Ser Gln Ile Ala Lys Gly Glu
465                 470                 475                 480
```

```
Asp Pro Ala Leu Gln Ile Cys Cys Gln Pro Ser Cys Thr Pro His Pro
            485                 490                 495

Val Cys Cys His Cys Pro Gly Ser Gln Ser
            500             505
```